(12) United States Patent
Haugan et al.

(10) Patent No.: US 8,681,211 B2
(45) Date of Patent: Mar. 25, 2014

(54) HIGH SPEED OPTICAL INSPECTION SYSTEM WITH ADAPTIVE FOCUSING

(75) Inventors: Carl E. Haugan, St. Paul, MN (US);
Steven K. Case, St. Louis Park, MN (US); Beverly Caruso, legal representative, St. Louis Park, MN (US);
Timothy A. Skunes, Mahtomedi, MN (US)

(73) Assignee: CyberOptics Corporation, Golden Valley, MN (US)

( * ) Notice: Subject to any disclaimer, the term of this patent is extended or adjusted under 35 U.S.C. 154(b) by 642 days.

(21) Appl. No.: 12/939,267

(22) Filed: Nov. 4, 2010

(65) Prior Publication Data

US 2011/0090333 A1     Apr. 21, 2011

Related U.S. Application Data

(63) Continuation-in-part of application No. 12/886,803, filed on Sep. 21, 2010, and a continuation-in-part of application No. 12/864,110, filed on Jan. 21, 2011, and a continuation-in-part of application No. 12/564,131, filed on Sep. 22, 2009.

(60) Provisional application No. 61/258,985, filed on Nov. 6, 2009, provisional application No. 61/244,616, filed on Sep. 22, 2009, provisional application No. 61/244,671, filed on Sep. 22, 2009.

(51) Int. Cl.
*H04N 9/47* (2006.01)
*G06K 9/00* (2006.01)

(52) U.S. Cl.
USPC .............................. 348/92; 382/150

(58) Field of Classification Search
USPC ................. 348/92, 126; 382/150; 250/559; 356/236; 359/626
See application file for complete search history.

(56) References Cited

U.S. PATENT DOCUMENTS

| 1,577,388 | A | 5/1923 | Twyman |
| 4,677,473 | A | 6/1987 | Okamoto |

(Continued)

FOREIGN PATENT DOCUMENTS

| CN | 1511248 A | 7/2004 |
| DE | 202008004430 | 1/2009 |

(Continued)

OTHER PUBLICATIONS

International Preliminary Report on Patentability for the related International application No. PCT/US2011/059040, dated Jan. 9, 2013.

(Continued)

*Primary Examiner* — Gims Philippe
(74) *Attorney, Agent, or Firm* — Christopher R. Christenson; Kelly, Holt & Christenson, PLLC

(57) ABSTRACT

An optical inspection system for inspecting a substrate is provided. The system includes an array of cameras configured to acquire a plurality of sets of images as the substrate and the array undergo relative motion with respect to each other. At least one focus actuator is operably coupled to each camera of the array of cameras to cause displacement of at least a portion of each camera that affects focus. A substrate range calculator is configured to receive at least portions of images from the array and to calculate range between the array of cameras and the substrate. A controller is coupled to the array of cameras and to the range calculator. The controller is configured to provide a control signal to each of the at least one focus actuator to adaptively focus each camera of the array during the relative motion.

28 Claims, 30 Drawing Sheets

(56) References Cited

U.S. PATENT DOCUMENTS

| | | | |
|---|---|---|---|
| 4,750,798 A | 6/1988 | Whitehead | |
| 4,795,913 A * | 1/1989 | Blessing et al. | 250/559.36 |
| 4,799,175 A | 1/1989 | Sano | |
| 4,896,211 A | 1/1990 | Hunt | |
| 4,978,224 A | 12/1990 | Kishimoto | |
| 4,993,826 A | 2/1991 | Yoder | |
| 5,039,868 A | 8/1991 | Kobayashi | |
| 5,058,178 A | 10/1991 | Ray | |
| 5,058,982 A | 10/1991 | Katzir | |
| 5,060,065 A | 10/1991 | Wasserman | |
| 5,086,397 A | 2/1992 | Schuster | |
| 5,153,668 A | 10/1992 | Katzir | |
| 5,245,421 A | 9/1993 | Robertson | |
| 5,260,779 A | 11/1993 | Wasserman | |
| 5,291,239 A | 3/1994 | Jackson | |
| 5,347,363 A | 9/1994 | Yamanaka | |
| 5,455,870 A | 10/1995 | Sepai | |
| 5,517,234 A | 5/1996 | Straayer | |
| 5,550,583 A | 8/1996 | Amir | |
| 5,684,530 A | 11/1997 | White | |
| 5,696,591 A | 12/1997 | Bilhorn | |
| 5,822,055 A | 10/1998 | Tsai | |
| 5,825,495 A | 10/1998 | Huber | |
| 5,880,772 A | 3/1999 | Kalnajs | |
| 6,020,957 A * | 2/2000 | Rosengaus et al. | 356/237.4 |
| 6,023,663 A | 2/2000 | Kim | |
| 6,175,107 B1 | 1/2001 | Juvinall | |
| 6,222,624 B1 | 4/2001 | Yonezawa | |
| 6,362,877 B1 | 3/2002 | Kobayashi | |
| 6,577,405 B2 | 6/2003 | Kranz | |
| 6,603,103 B1 | 8/2003 | Ulrich et al. | 250/205 |
| 6,633,375 B1 | 10/2003 | Veith | |
| 6,750,899 B1 | 6/2004 | Fishbaine et al. | 348/126 |
| 6,757,966 B2 | 7/2004 | Inoue | |
| 6,850,855 B2 | 2/2005 | Kawai | |
| 7,019,826 B2 | 3/2006 | Vook | |
| 7,027,639 B2 * | 4/2006 | Fishbaine | 382/150 |
| 7,075,565 B1 * | 7/2006 | Raymond et al. | 348/126 |
| 7,310,438 B2 | 12/2007 | Prince | |
| 7,372,632 B2 * | 5/2008 | Lizotte | 359/626 |
| 7,394,084 B2 | 7/2008 | Kuriyama et al. | 250/559.34 |
| 7,460,219 B2 | 12/2008 | Jung | |
| 7,828,472 B2 | 11/2010 | Liu et al. | |
| 8,098,372 B2 | 1/2012 | Eitan et al. | 356/237.2 |
| 2002/0089664 A1 | 7/2002 | Shibata | |
| 2003/0039388 A1 | 2/2003 | Ulrich et al. | |
| 2003/0110610 A1 | 6/2003 | Duquette et al. | |
| 2003/0179369 A1 | 9/2003 | Feldman | |
| 2003/0227618 A1 | 12/2003 | Some | |
| 2004/0156539 A1 | 8/2004 | Jansson | |
| 2005/0219518 A1 | 10/2005 | Korngut | |
| 2005/0259245 A1 | 11/2005 | Cemic | |
| 2006/0028320 A1 | 2/2006 | Osaka | |
| 2006/0062013 A1 | 3/2006 | Imade | |
| 2011/0069154 A1 | 3/2011 | Case | |
| 2011/0069507 A1 | 3/2011 | Haugan | |
| 2011/0069878 A1 | 3/2011 | Case | |
| 2011/0075156 A1 | 3/2011 | Patel et al. | 356/603 |
| 2011/0102575 A1 | 5/2011 | Case et al. | |
| 2011/0175997 A1 | 7/2011 | Case et al. | |
| 2012/0133920 A1 | 5/2012 | Skunes et al. | 356/23 |
| 2012/0327215 A1 | 12/2012 | Case et al. | |

FOREIGN PATENT DOCUMENTS

| | | |
|---|---|---|
| EP | 0301255 | 2/1989 |
| EP | 0935774 | 8/1999 |
| EP | 0994646 | 4/2000 |
| EP | 1578186 | 9/2005 |
| EP | 1694109 A2 | 8/2006 |
| GB | 2271683 | 4/1994 |
| GB | 2417072 | 2/2006 |
| GB | 2444409 | 6/2008 |
| JP | 61134718 | 6/1986 |
| JP | 6229875 | 12/1987 |
| JP | 63011842 | 1/1988 |
| JP | 02268260 | 11/1990 |
| JP | 08327561 | 12/1996 |
| JP | 2002271099 A | 9/2002 |
| JP | 2006324599 | 11/2006 |
| WO | WO 98/19200 | 5/1998 |
| WO | WO 00/26640 | 5/2000 |
| WO | WO 00/38494 | 6/2000 |
| WO | WO 01/96839 A1 | 12/2001 |
| WO | WO 00/26640 | 5/2005 |
| WO | WO 2009/014940 | 1/2009 |

OTHER PUBLICATIONS

International Preliminary Report on Patentability for the corresponding International application No. PCT/US2010/055452, dated Feb. 22, 2013.
Search Report and Written Opinion for the related International application No. PCT/US2012/065838, dated Feb. 14, 2013.
Written Opinion for International application No. PCT/US2010/049617 dated Feb. 14, 2012.
Invitation to Pay Additional Fees from International patent application No. PCT/US2011/059040 dated Mar. 15, 2012.
Notification of Transmittal of International Preliminary Report on Patentability for the International application No. PCT/US10/49617 dated Aug. 24, 2012.
Notification of transmittal of the International Search Report and the Written Opinion for International application No. PCT/US2011/059040 dated Jul. 20, 2012.
Martin, "A practical Guide to Machine Vision Lighting", Advance Illumination, Rochester, VT, United States, Oct. 2007.
Scharstein and Szeliski, "A Taxonomy and Evaluation of Dense Two-Frame Stereo Correspondence Algorithms"Microsoft Research, Microsoft Corporation, Redmond, WA, Apr. 2002.
Smith, "Modern Optical Engineering: The Design of Optical Systems", 4th ed. New York: McGraw-Hill, 2008.
Kang, Web, Zitinick, and Takeo, "A Multibaseline Stereo System with Active Illumination and Real-time Image Acquisition.", Jun. 1995.
Collins, "A Space-Sweep Approach to True Multi-Image Matching" University of Massachusetts, Amherst, MA, Jun. 1996.
CyberOptics, "Flex Ultra TM HR, Automated Optical Inspection", CyberOptics Corporation 2007.
Notification of transmittal of the International Search Report and the Written Opinion for International application No. PCT/US2009/031744 dated May 18, 2009.
Notification of transmittal of the International Search Report and the Written Opinion for International application No. PCT/US2010/049619 dated Dec. 8, 2010.
Notification of transmittal of the International Search Report and the Written Opinion for International application No. PCT/US2010/049617 dated Dec. 8, 2010.
Notification of transmittal of the International Search Report and the Written Opinion for International application No. PCT/US2010/055452 dated Jan. 17, 2011.
U.S. Appl. No. 12/864,110, filed Jul. 22, 2010.
U.S. Appl. No. 12/940,214, filed Nov. 5, 2010.
Office Action from counterpart Chinese Patent Application No. 201080050021.4, dated Nov. 18, 2013, 16 Pages.

* cited by examiner

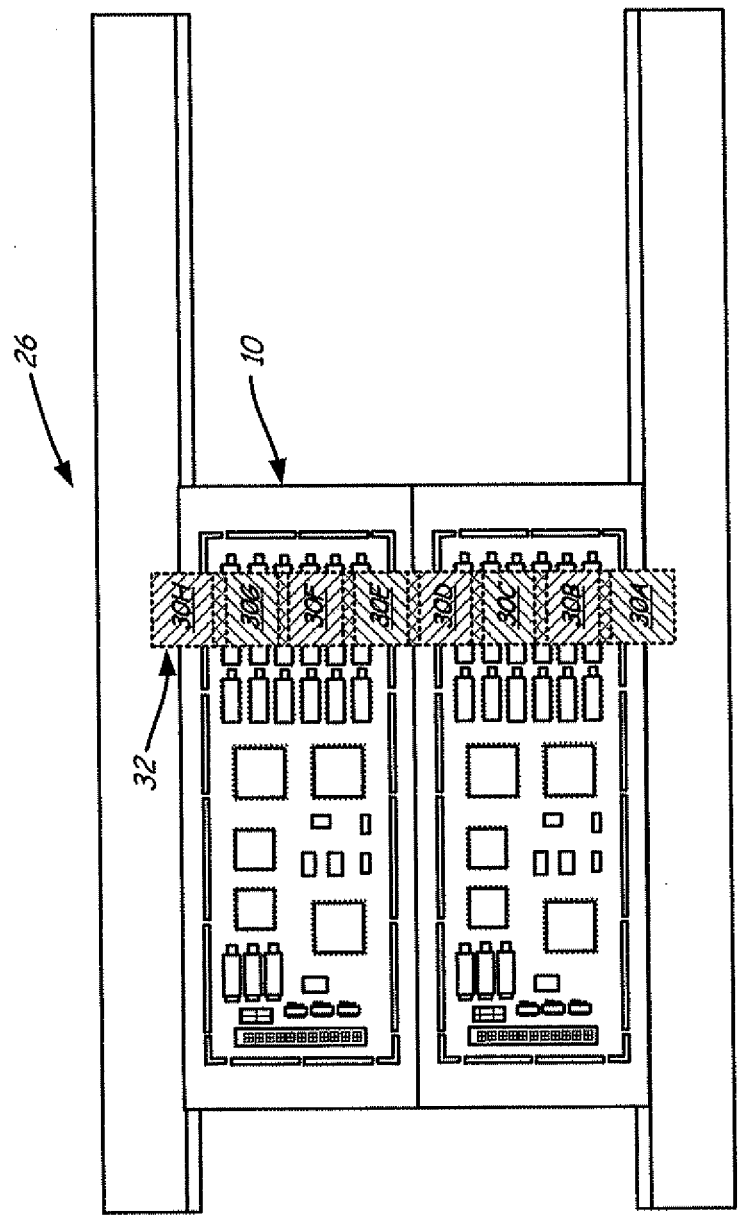
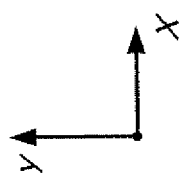
FIG. 4

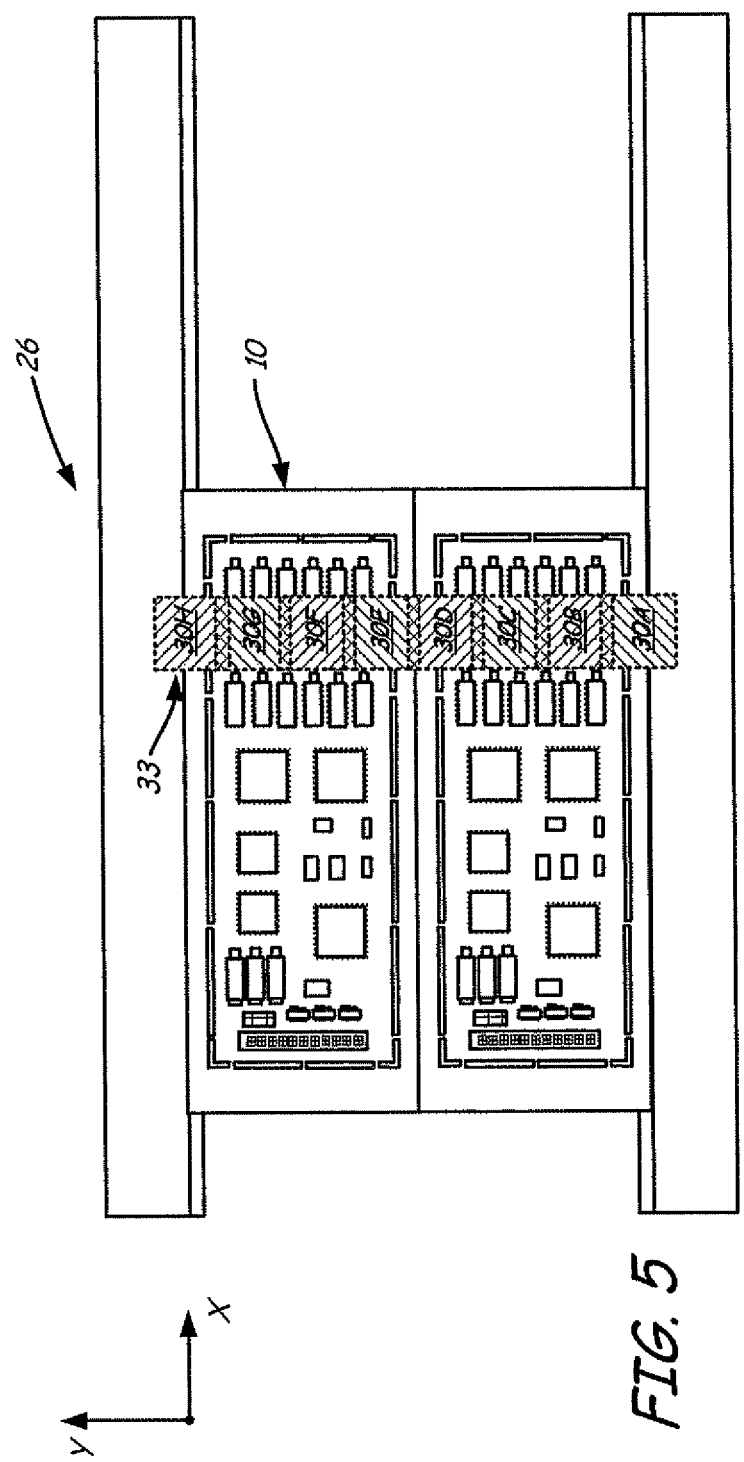

HIGH SPEED OPTICAL INSPECTION SYSTEM WITH ADAPTIVE FOCUSING

CROSS-REFERENCE TO RELATED APPLICATION

The present application is based on and claims the benefit of U.S. Provisional Application Ser. No. 61/258,985, filed Nov. 6, 2009; and the present application is a Continuation-In-Part application of U.S. patent application Ser. No. 12/886,803, filed Sep. 21, 2010, which application is based on and claims the benefit of U.S. Provisional Application Ser. No. 61/244,616, filed Sep. 22, 2009 and U.S. Provisional Application Ser. No. 61/244,671, filed on Sep. 22, 2009; and is a Continuation-In-Part application of U.S. patent application Ser. No. 12/864,110 filed Jul. 22, 2010; and is a Continuation-In-Part application of U.S. patent application Ser. No. 12/564,131, filed Sep. 22, 2009. All applications listed above are herein incorporated by reference in their entireties.

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Automated electronics assembly machines are often used in the manufacture of printed circuit boards, which are used in various electronic devices. Such automatic electronic assembly machines are often used to process other devices that are similar to printed circuit boards. For example, the manufacture of photovoltaic cells (solar cells) often uses similar machines for printing conductive traces. Regardless of the substrate being processed, the process itself is generally required to operate quite swiftly. Rapid or high speed manufacturing ensures that costs of the completed substrate are minimized. However, the speed with which the substrates are manufactured must be balanced by the acceptable level of scrap or defects caused by the process. Printed circuit boards, for example, can be extremely complicated and any one board may have a vast number of small components and features and consequently a vast number of electrical connections. Furthermore, printed circuit board substrates may acquire a significant amount of warp as they progress through the various assembly steps. Since such printed circuit boards can be quite expensive and/or be used in expensive equipment, it is important that they be produced accurately and with high quality, high reliability, and minimum scrap. Unfortunately, because of the manufacturing methods available, some level of scrap and rejects still occurs. Typical faults on printed circuit boards include inaccuracy of placement of components on the board, which might mean that the components are not correctly electrically connected in the board. Another typical fault occurs when an incorrect component is placed at a given location on a circuit board. Additionally, the component might simply be absent, or it may be placed with incorrect electrical polarity. Further, other errors may prohibit, or otherwise inhibit, electrical connections between one or more components, and the board. Further still, if there are insufficient solder paste deposits, this can lead to poor connections. Additionally, if there is too much solder paste, such a condition can lead to short circuits, and so on.

In view of all of these industry demands, a need has arisen for automated optical inspection systems. These systems can receive a substrate, such as a printed circuit board, either immediately after placement of the components upon the printed circuit board and before wave soldering, or post reflow. Typically, the systems include a conveyor that is adapted to move the substrate under test through an optical field of view that acquires one or more images and analyzes those images to automatically draw conclusions about components on the substrate and/or the substrate itself. One example of such device is sold under the trade designation Flex Ultra™ HR available from CyberOptics Corporation, of Golden Valley, Minn. However, as described above, the industry continues to pursue faster and faster processing, and accordingly faster automated optical inspection is desired. Moreover, given the wide array of various objects that the system may be required to inspect, it would be beneficial to provide an automated optical inspection system that was not only faster than previous systems, but better able to provide valuable inspection data relative to a wider variety of components, substrates, or inspection criteria.

SUMMARY

An optical inspection system for inspecting a substrate is provided. The system includes an array of cameras configured to acquire a plurality of sets of images as the substrate and the array undergo relative motion with respect to each other. At least one focus actuator is operably coupled to each camera of the array of cameras to cause displacement of at least a portion of each camera that affects focus. A substrate range calculator is configured to receive at least portions of images from the array and to calculate range between the array of cameras and the substrate. A controller is coupled to the array of cameras and to the range calculator. The controller is configured to provide a control signal to each of the at least one focus actuator to adaptively focus each camera of the array during the relative motion.

BRIEF DESCRIPTION OF THE DRAWINGS

FIG. 4 is a top plan view of a transport conveyor, printed circuit board, and a camera array field of view acquired with a first illumination field type.

FIG. 5 is a top plan view of a transport conveyor, printed circuit board, and a camera array field of view acquired with a second illumination field type.

DETAILED DESCRIPTION OF ILLUSTRATIVE EMBODIMENTS

Figure 1:
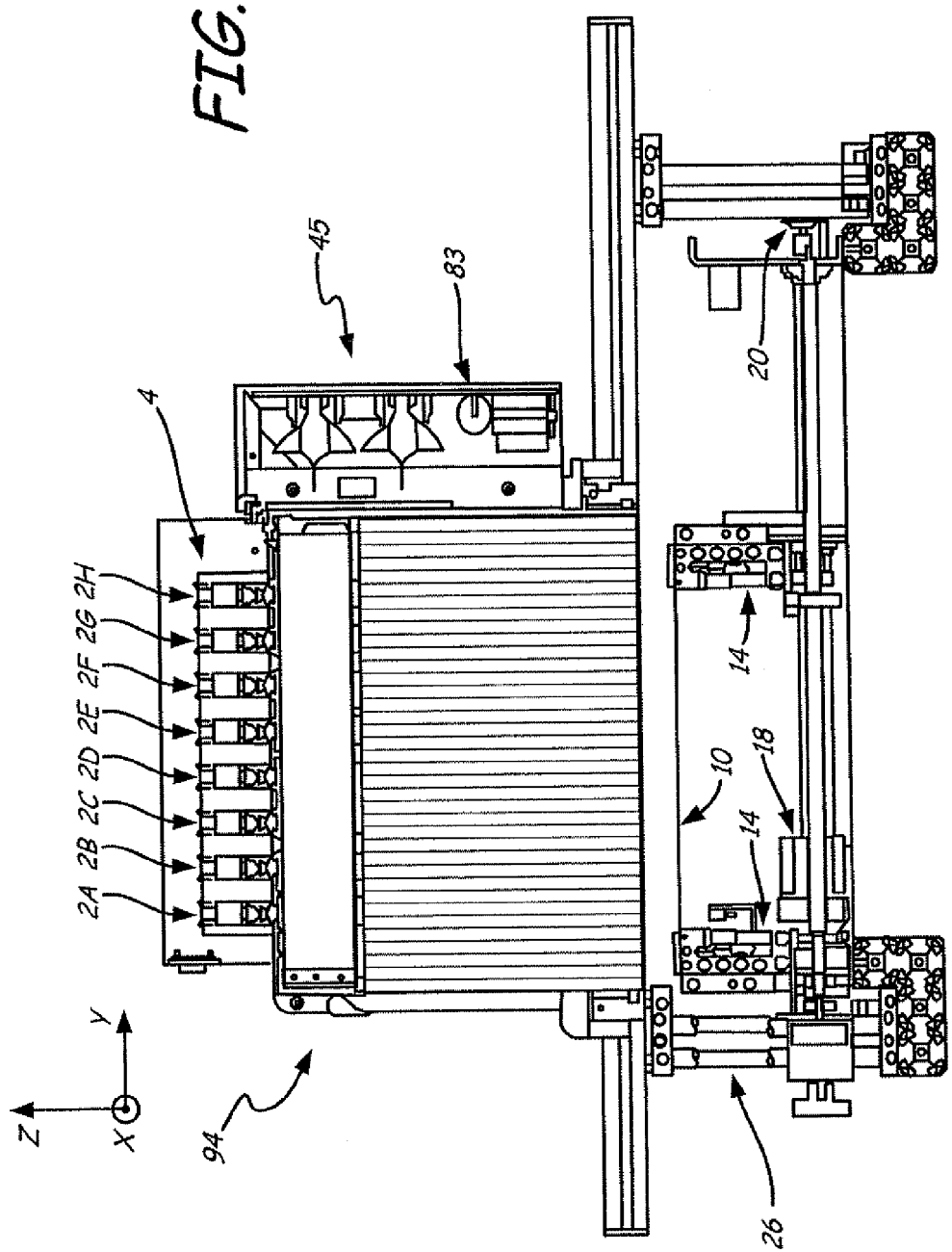
FIG. 1 is a cross-sectional elevation view of an automated high speed optical inspection system with a camera array and compact, integrated illuminator in accordance with embodiment of the present invention.

Embodiments of the present invention will generally be described with respect to the figures. A number of reference numerals are used to refer to the various features of the figures. For clarity, a listing of the various reference numerals follows.

2—camera
4—camera array
9—autofocus actuator
10—printed circuit board
11—small workpiece
14—belt
16—range calculator
17—structured illumination projector
18—motor
20—encoder
22—programmable logic controller
24—panel sensor
26—workpiece transport conveyor
27—clamping conveyor
28—conveyor clamp
30—camera field of view
32—camera array field of view
33—camera array field of view
34—camera array field of view
35—camera array field of view
39—camera array field of view
41—illuminator
42—illuminator
43—illuminator
44—illuminator
45—illuminator
46—LED
48—linear light source
50—aperture
52—diffuser plate
54—mirror
57—mixing chamber
58—top aperture plate
60—light source
62—collimated light ray bundle
64—light pipe
65—light pipe illuminator
66—light pipe side wall
67—mirrors
68—light pipe exit aperture
69—light pipe entrance aperture
70—reflective surface
71—inspection application program
72—conveyor interface
76—system computer
80—main electronics board
82—image memory
83—strobe assembly
84—strobe board
86—strobe monitor
87—flash lamp
88—flash lamp
92—inspection system
93—optical inspection sensor
94—optical inspection sensor
99—optical inspection sensor
150—flowchart step
152—flowchart step
154—flowchart step
156—flowchart step
158—flowchart step
160—flowchart step
162—flowchart decision step
164—flowchart step 166—flowchart step
168—flowchart step
170—flowchart step
174—flowchart step
176—flowchart step
178—flowchart step
180—flowchart step
182—flowchart decision step
184—rails
185—belt
186—support
187—support
188—slide mechanism
189—stage
190—motor
191—motor Embodiments of the present invention generally provide an inspection system and method with high speed acquisition of multiple illumination images without the need for expensive and sophisticated motion control hardware. Processing of the images acquired with different illumination types may appreciably enhance the inspection results. Also, adaptive focusing facilitates high resolution imagery when a workpiece is warped.

FIG. 1 shows a cross-sectional elevation view of a system for generating high contrast, high speed digital images of a workpiece that are suitable for automated inspection, in accordance with an embodiment of the present invention. Camera array 4 consists of cameras 2A through 2H preferably arranged at regular intervals. Each camera 2A through 2H simultaneously images and digitizes a rectangular area on a workpiece or substrate, such as printed circuit board 10, while the workpiece undergoes relative movement with respect to cameras 2A through 2H. Illuminator 45 provides a series of pulsed, short duration illumination fields referred to as strobed illumination. The short duration of each illumination field effectively "freezes" the image of printed circuit board 10 to suppress motion blurring. Two or more sets of images for each location on printed circuit board 10 are generated by camera array 4 with different illumination field types for each exposure. Depending on the particular features on printed circuit board that need to be inspected, the inspection results may be appreciably enhanced by joint processing of the reflectance images generated with different illumination field types. Further details of illuminator 45 are provided in the discussion of FIGS. 21 and 22.

Workpiece transport conveyor 26 translates printed circuit board 10 in the X direction in a nonstop mode to provide high speed imaging of printed circuit board 10 by camera array 4. Conveyor 26 includes belts 14 which are driven by motor 18. Optional encoder 20 measures the position of the shaft of motor 18 hence the approximate distance traveled by printed circuit board 10 can be calculated. Other methods of measuring and encoding the distance traveled of printed circuit board 10 include time-based, acoustic or vision-based encoding methods. By using strobed illumination and not bringing printed circuit board 10 to a stop, the time-consuming transport steps of accelerating, decelerating, and settling prior to imaging by camera array 4 are eliminated. It is believed that the time required to entirely image a printed circuit board 10 of dimensions 210 mm×310 mm can be reduced from 11 seconds to 4 seconds using embodiments of the present invention compared to coming to a complete stop before imaging.

Figure 2:
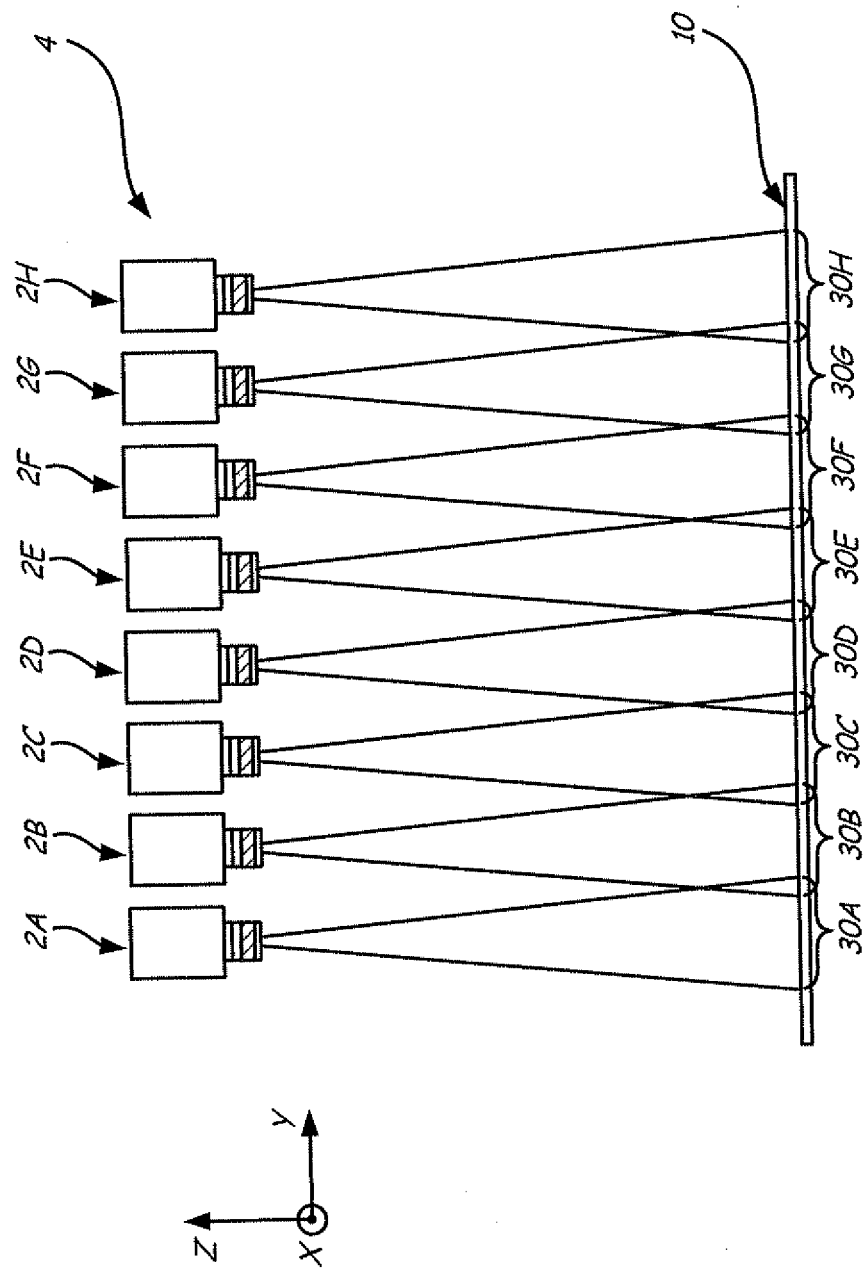
FIG. 2 is a diagrammatic elevation view of a plurality of cameras having overlapping fields of view in accordance with an embodiment of the present invention.

FIG. 2 shows the Y dimension location of each field of view 30A through 30H on printed circuit board 10 that is imaged by cameras 2A through 2H, respectively. There is a slight overlap between adjacent fields of view in order to completely image all locations on printed circuit board 10. During the inspection process, the images of discrete fields of view 30A through 30H are digitally merged, or stitched, into one continuous image in the overlap regions. Example camera array 4 is shown in FIGS. 1 and 2 arranged as a single dimensional array of discrete cameras. As shown, cameras 2A-2H are configured to image in a non-telecentric manner. This has the advantage that the fields of view 30A through 30H can be overlapped. However, the magnification, or effective resolution, of a non-telecentric imaging system will change as printed circuit 10 and its features are positioned closer or further away from cameras 2A-2H. Effects of circuit board 10 warpage, thickness variations and other camera alignment errors can be compensated by image stitching. In another embodiment, the camera array may be arranged in a two dimensional array. For example, the discrete cameras may be arranged into a camera array of two columns of four cameras where adjacent fields of view overlap. Other arrangements of the camera array may be advantageous depending on cost, speed, and performance goals of the inspection system, including arrays where the fields of view do not overlap. For example, a staggered array of cameras with telecentric imaging systems may be used.

Figure 3:
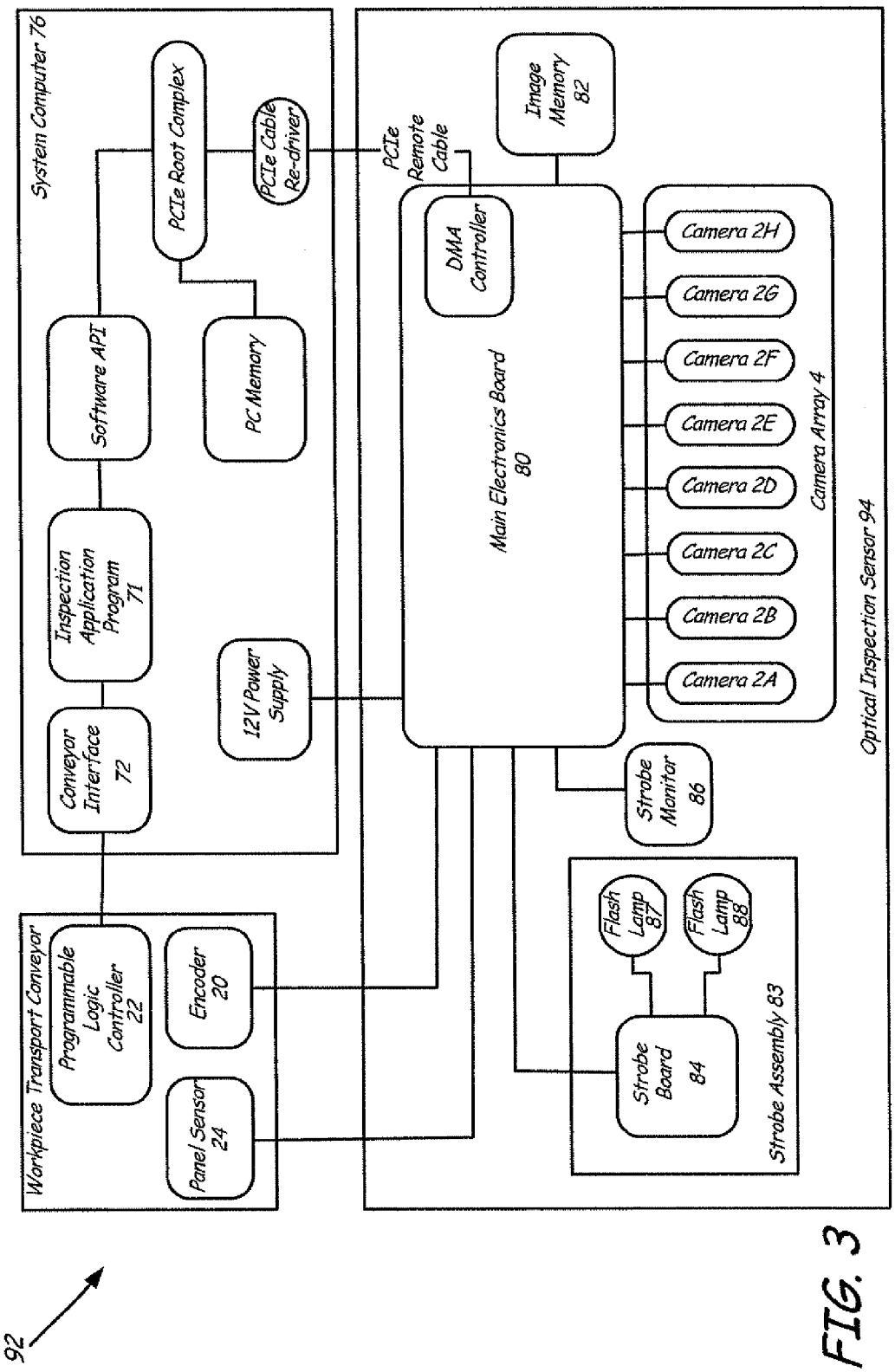
FIG. 3 is a system block diagram of an inspection system in accordance with an embodiment of the present invention.

FIG. 3 is a block diagram of inspection system 92. Inspection application program 71 preferably executes on system computer 76. Inputs into inspection program 71 include the type of printed circuit board 10, CAD information describing the location and types of components on printed circuit board 10, the features on printed circuit board 10 to be inspected, lighting and camera calibration data, the transport conveyor 26 direction, et cetera. Inspection program 71 configures programmable logic controller 22 via conveyor interface 72 with the transport direction, velocity, and width of printed circuit board 10. Inspection program 71 also configures main electronics board 80 via PCI express interface with the number of encoder 20 counts between each subsequent image acquisition of camera array 4. Alternatively, a time-based image acquisition sequence may be executed based on the known velocity of printed circuit board 10. Inspection program 71 also programs or otherwise sets appropriate configuration parameters into cameras 2A-2H prior to an inspection as well as strobe board 84 with the individual flash lamp output levels.

Panel sensor 24 senses the edge of printed circuit board 10 as it is loaded into inspection system 92 and this signal is sent to main board 80 to begin an image acquisition sequence. Main board 80 generates the appropriate signals to begin each image exposure by camera array 4 and commands strobe board 84 to energize the appropriate flash lamps 87 and 88 at the proper time. Strobe monitor 86 senses a portion of light emitted by flash lamps 87 and 88 and this data may be used by main electronics board 80 to compensate image data for slight flash lamp output variations. Image memory 82 is provided and preferably contains enough capacity to store all images generated for at least one printed circuit board 10. For example, in one embodiment, each camera in the array of cameras has a resolution of about 5 megapixels and memory 82 has a capacity of about 2.0 gigabytes. Image data from cameras 2A-2H may be transferred at high speed into image memory buffer 82 to allow each camera to be quickly prepared for subsequent exposures. This allows the printed circuit board 10 to be transported through inspection system 92 in a nonstop manner and generate images of each location on printed circuit board 10 with at least two different illumination field types. The image data may begin to be read out of image memory into PC memory over a high speed electrical interface such as PCI Express (PCIe) as soon as the first images are transferred to memory 82. Similarly, inspection program 71 may begin to compute inspection results as soon as image data is available in PC memory.

The image acquisition process will now be described in further detail with respect to FIGS. 4-6.

FIG. 4 shows a top plan view of transport conveyor 26 and printed circuit board 10. Cameras 2A-2H image overlapping fields of view 30A-30H, respectively, to generate effective field of view 32 of camera array 4. Field of view 32 is acquired with a first strobed illumination field type. Printed circuit board 10 is transported by conveyor 26 in a nonstop manner in the X direction. Printed circuit board 10 preferably travels at a velocity that varies less than five percent during the image acquisition process, although larger velocity variations and accelerations may be accommodated.

In one preferred embodiment, each field of view 30A-30H has approximately 5 million pixels with a pixel resolution of 17 microns and an extent of 33 mm in the X direction and 44 mm in the Y direction. Each field of view 30A-30H overlaps neighboring fields of view by approximately 4 mm in the Y direction so that center-to-center spacing for each camera 2A-2H is 40 mm in the Y direction. In this embodiment, camera array field of view 32 has a large aspect ratio in the Y direction compared to the X direction of approximately 10:1.

FIG. 5 shows printed circuit board 10 at a location displaced in the positive X direction from its location in FIG. 4. For example, printed circuit board 10 may be advanced approximately 14 mm from its location in FIG. 4. Effective field of view 33 is composed of overlapping fields of view 30A-30H and is acquired with a second illumination field type.

Figure 6A:
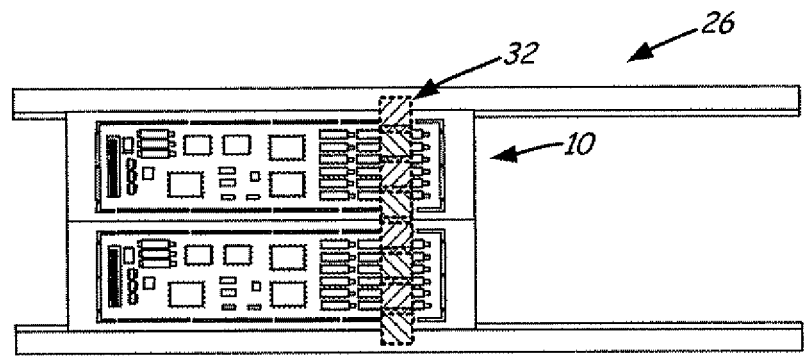
FIGS. 6A-6D illustrate a workpiece and camera array fields of view acquired at different positions and under alternating first and second illumination field types in accordance with an embodiment of the present invention.
Figure 6B:
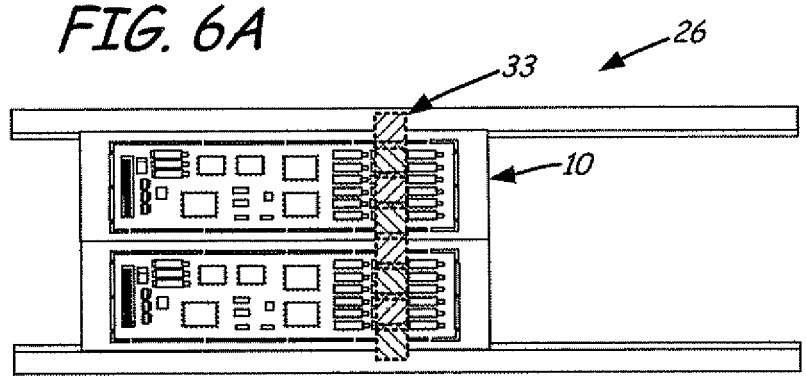
Figure 6C:
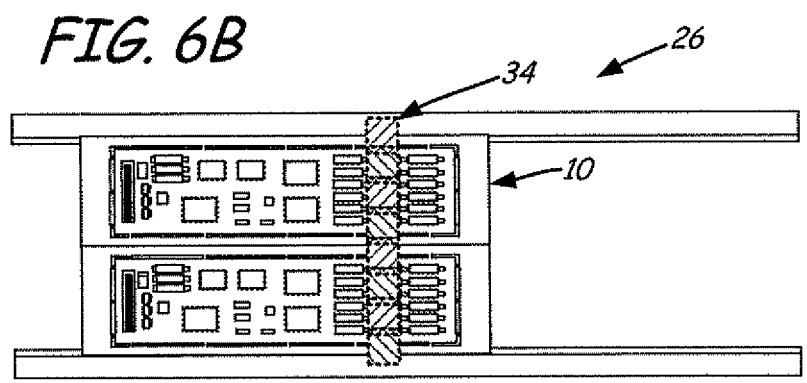
Figure 6D:
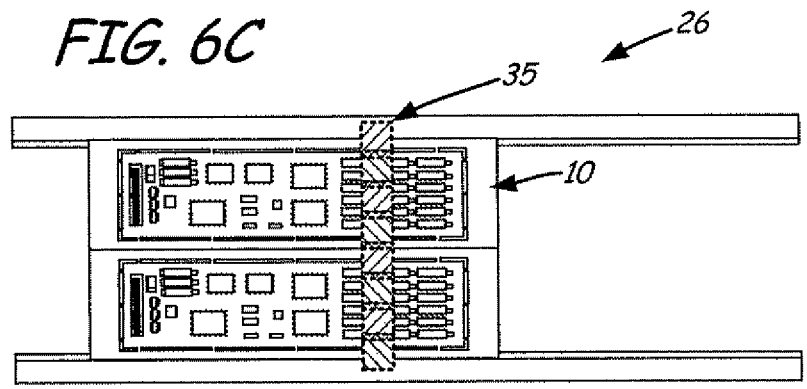

FIGS. 6A-6D show a time sequence of camera array fields of view 32-35 acquired with alternating first and second illumination field types. It is understood that printed circuit board 10 is traveling in the X direction in a nonstop fashion. FIG. 6A shows printed circuit board 10 at one X location during image acquisition for the entire printed circuit board 10. Field of view 32 is acquired with a first strobed illumination field type as discussed with respect to FIG. 4. FIG. 6B shows printed circuit board 10 displaced further in the X direction and field of view 33 acquired with a second strobed illumination field type as discussed with respect to FIG. 5. FIG. 6C shows printed circuit board 10 displaced further in the X direction and field of view 34 acquired with the first illumination field type and FIG. 6D shows printed circuit board 10 displaced further in the X direction and field of view 35 acquired with the second illumination field type.

There is a small overlap in the X dimension between field of views 32 and 34 in order to have enough overlapping image information in order to register and digitally merge, or stitch together, the images that were acquired with the first illumination field type. There is also small overlap in the X dimension between field of views 33 and 35 in order to have enough overlapping image information in order to register and digitally merge the images that were acquired with the second illumination field type. In the embodiment with fields of view 30A-30H having extents of 33 mm in the X direction, it has been found that an approximate 5 mm overlap in the X direction between field of views acquired with the same illumination field type is effective. Further, an approximate 14 mm displacement in the X direction between fields of view acquired with different illumination types is preferred.

Images of each feature on printed circuit board 10 may be acquired with more than two illumination field types by increasing the number of fields of view collected and ensuring sufficient image overlap in order to register and digitally merge, or stitch together, images generated with like illumination field types. Finally, the stitched images generated for each illumination type may be registered with respect to each other. In a preferred embodiment, workpiece transport conveyor 26 has lower positional accuracy than the inspection requirements in order to reduce system cost. For example, encoder 20 may have a resolution of 100 microns and conveyor 26 may have positional accuracy of 0.5 mm or more. Image stitching of fields of view in the X direction compensates for positional errors of the circuit board 10.

It is desirable that each illumination field is spatially uniform and illuminates from consistent angles. It is also desirable for the illumination system to be compact and have high efficiency. Limitations of two prior art illumination systems, linear light sources and ring lights, will be discussed with reference to FIGS. 7-9. Linear light sources have high efficiency, but poor uniformity in the azimuth angle of the projected light. Ring light sources have good uniformity in the azimuth angle of the projected light, but are not compact and have poor efficiency when used with large aspect ratio camera arrays.

Figure 7:
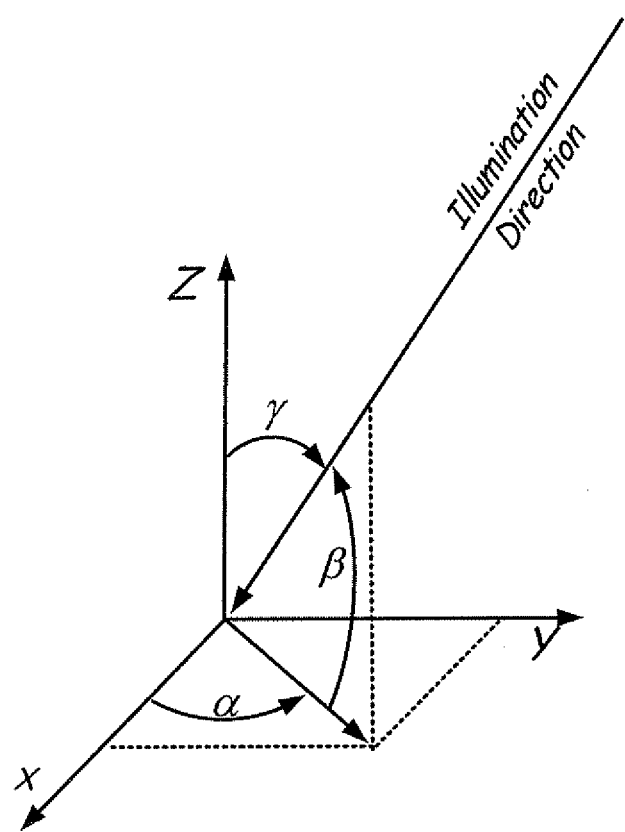
FIG. 7 is a coordinate system for defining illumination direction.

FIG. 7 defines a coordinate system for illumination. Direction Z is normal to printed circuit board 10 and directions X and Y define horizontal positions on printed circuit board 10 or other workpiece. Angle $\beta$ defines the elevation angle of the illumination. Angle $\gamma$ redundantly defines the illumination ray angle with respect to normal. Angle $\alpha$ is the azimuth angle of the ray. Illumination from nearly all azimuth and elevation angles is termed cloudy day illumination. Illumination predominantly from low elevation angles, $\beta$, near horizontal is termed dark field illumination. Illumination predominantly from high elevation angles, $\beta$, near vertical is termed bright field illumination. A good, general purpose, illumination system will create a light field with uniform irradiance across the entire field of view (spatial uniformity) and will illuminate from consistent angles across the entire field of view (angle uniformity).

Figure 8:
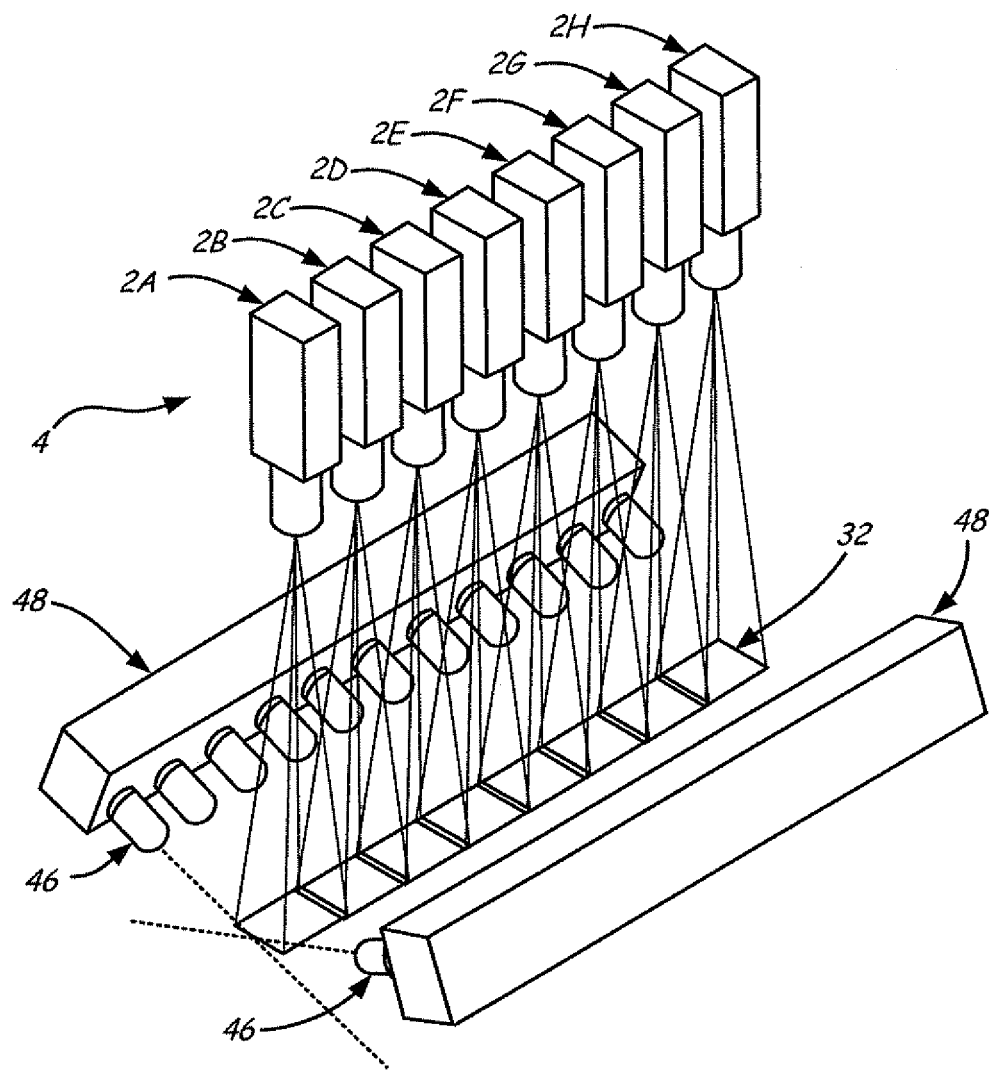
FIG. 8 is a perspective view of a known linear line source illuminating a camera array field of view.

FIG. 8 shows known linear light sources 48 illuminating camera array field of view 32. Linear light source 48 can use an array of LEDs 46 to efficiently concentrate light on a narrow rectangular field of view 32. A disadvantage of using linear light sources 48 is that although the target receives symmetrical illumination from the two directions facing the sources, no light is received from the directions facing the long axis of the FOV.

Figure 9:
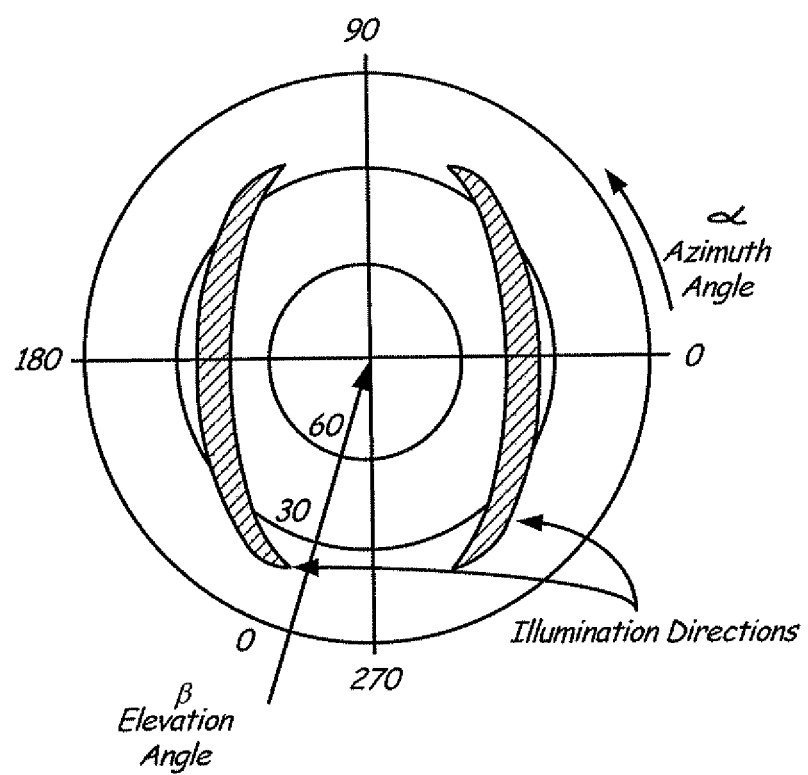
FIG. 9 is a polar plot of the illumination directions of the illuminator shown in FIG. 8.

FIG. 9 is a two axis polar plot showing illumination directions for the two linear light sources 48. The polar plot shows that strong illumination is received by camera array field of view 32 from the direction nearest to light sources 48 (at 0 and 180 degree azimuth angles) and that no illumination received from the 90 and 270 degrees azimuth angle. As the azimuth angle varies between 0 and 90 the source elevation angle drops and the source subtends a smaller angle so less light is received. Camera array field of view 32 receives light which varies in both intensity and elevation angle with azimuth angle. The linear light sources 48 efficiently illuminate field of view 32, but with poor uniformity in azimuth angle. In contrast, known ring lights have good uniformity in azimuth, but must be made large in order to provide acceptable spatial uniformity for large aspect ratio camera field of 32.

Although a ring light could be used to provide acceptable uniformity in azimuth, the ring light would need to be very large to provide acceptable spatial uniformity for camera field of view 32 of approximately 300 mm in the Y direction. For typical inspection applications, it is believed that the ring light would need to be over 1 meter in diameter to provide sufficient spatial uniformity. This enormous ring fails to meet market needs in several respects: the large size consumes valuable space on the assembly line, the large light source is expensive to build, the illumination angles are not consistent across the working field, and it is very inefficient—the light output will be scattered over a significant fraction of the 1 meter circle while only a slim rectangle of the board is actually imaged.

An optical device, referred to as a light pipe, can be used to produce a very uniform light field for illumination. For example, U.S. Pat. No. 1,577,388 describes a light pipe used to back illuminate a film gate. Conventional light pipes, however, need to be physically long to provide uniform illumination.

Figure 10:
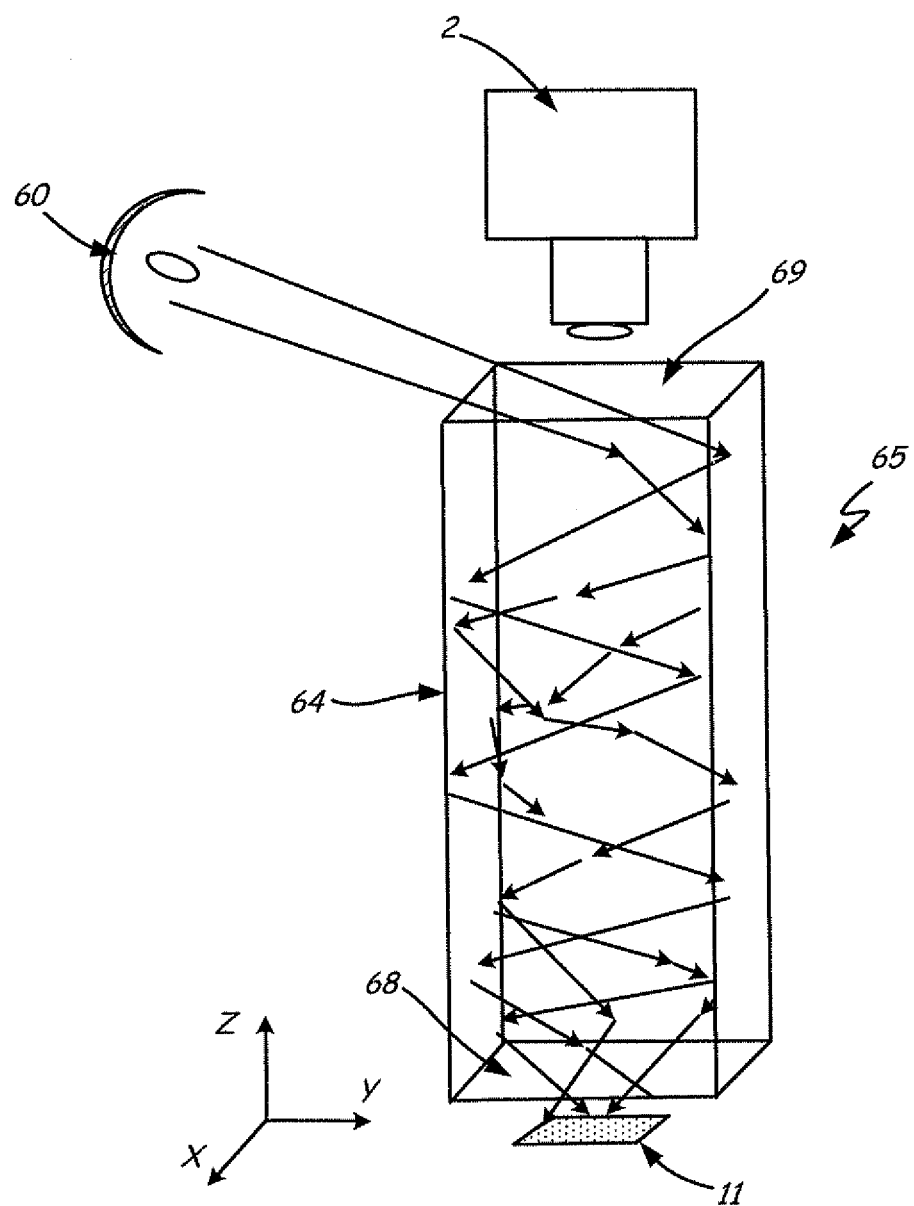
FIG. 10 is a perspective view of an example hollow light pipe illuminator in accordance with an embodiment of the present invention.
Figure 11:
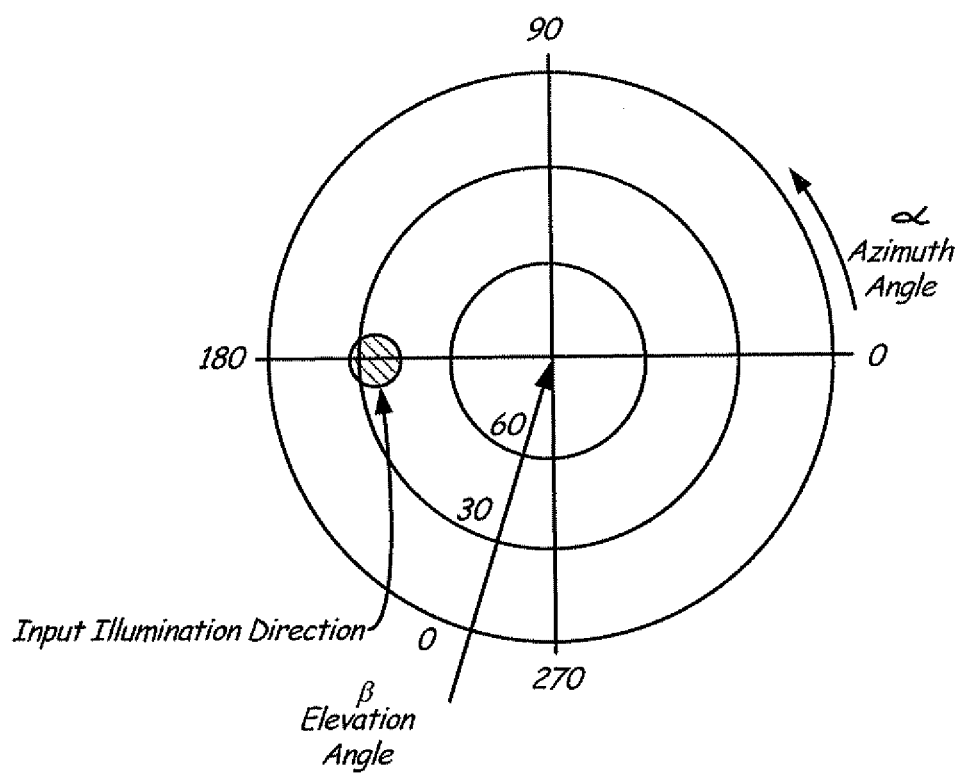
FIG. 11 is a polar plot of the input illumination direction of the illuminator shown in FIG. 10.
Figure 12:
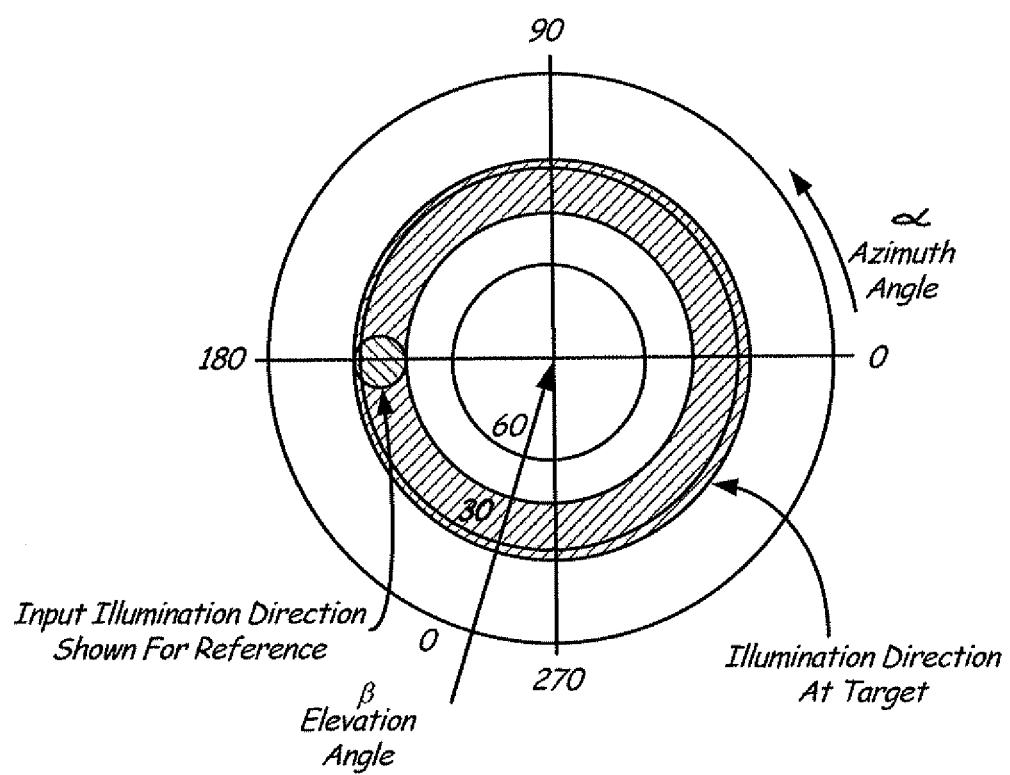
FIG. 12 is a polar plot of the output illumination directions of the illuminator shown in FIG. 10.

A brief description of light pipe principles is provided with respect to FIGS. 10-12. Embodiments of the present invention are then described with respect to FIGS. 13-17 that significantly reduce the length of a light pipe required for uniform illumination. In one embodiment, the interior walls of the light pipe are constructed with reflective materials that scatter light in only one direction. In another embodiment of the present invention, the light pipes are configured with input and output ports that allow simple integration of a camera array to acquire images of a uniformly and efficiently illuminated workpiece.

FIG. 10 shows illuminator 65 which consists of light source 60 and light pipe 64. Hollow box light pipe 64 which, when used as described, will generate a uniform dark field illumination pattern. Camera 2 views workpiece 11 down the length of light pipe 64 through apertures 67 and 69 at the ends of the light pipe. A light source 60, for example an arc in a parabolic reflector, is arranged such that it projects light into the entrance aperture 67 of light pipe 64 with internally reflecting surfaces such that light descends at the desired elevation angle. Alternatively a lensed LED or other source may be used as long as the range of source elevation angles matches the desired range of elevation angles at workpiece 11. The light source may be either strobed or continuous. The fan of rays from light source 60 proceeds across the pipe and downward until it strikes one of the side walls. The ray fan is split and spread in azimuth at the corners of the pipe but the elevation angle is preserved. This expanded ray fan then spreads out, striking many different side wall sections where it is further spread and randomized in azimuth angle and largely unchanged in elevation angle. After a number of reflections all azimuth angles are present at exit aperture 68 and workpiece 11. Therefore all points on the target are illuminated by light from all azimuth angles but only those elevation angles present in the original source. In addition, the illumination field at workpiece 11 is spatially uniform. Note that the lateral extent of light pipe 64 is only slightly larger than the field of view in contrast to the required size of a ring light for the condition of spatially uniform illumination.

FIG. 11 shows the polar plot of the illumination direction at the source, a nearly collimated bundle of rays from a small range of elevation and azimuth angles.

FIG. 12 is a polar plot of the rays at workpiece 11 and the angular spread of the source is included for comparison. All azimuth angles are present at workpiece 11 and the elevation angles of the source are preserved.

As the elevation angle of light exiting illuminator 65 is the same as those present in the source 60, it is relatively easy to tune those angles to specific applications. If a lower elevation illumination angle is desired then the source may be aimed closer to the horizon. The lower limit to the illumination angle is set by the standoff of the light pipe bottom edge as light cannot reach the target from angles below the bottom edge of the light pipe. The upper limit to the illumination elevation angle is set by the length of light pipe 66 since several reflections are required to randomize, or homogenize, the illumination azimuth angle. As elevation angle is increased there will be fewer bounces for a given length light pipe 64 before reaching workpiece 11.

The polygonal light pipe homogenizer only forms new azimuth angles at its corners, therefore many reflections are needed to get a uniform output If all portions of the light pipe side walls could spread or randomize the light pattern in the azimuth direction, then fewer reflections would be required and the length of the light pipe in the Z direction could be reduced making the illuminator shorter and/or wider in the Y direction.

Figure 13:
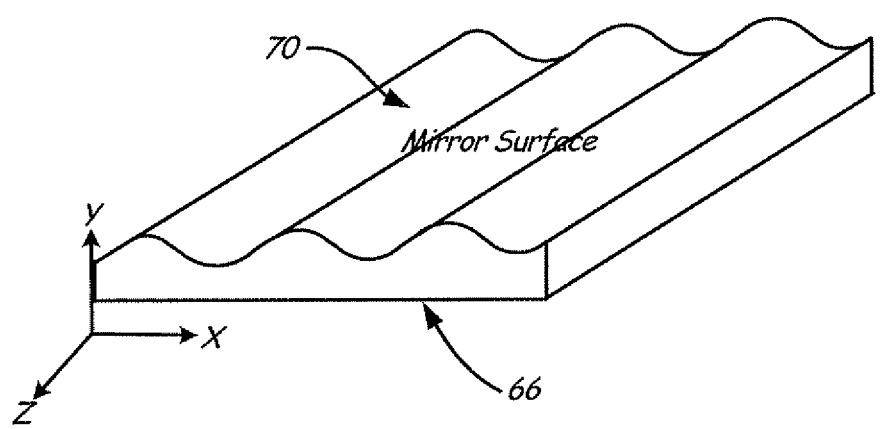
FIG. 13 is a perspective view of a reflective surface of a light pipe wall in accordance with an embodiment of the present invention.
Figures 14A, 14B:
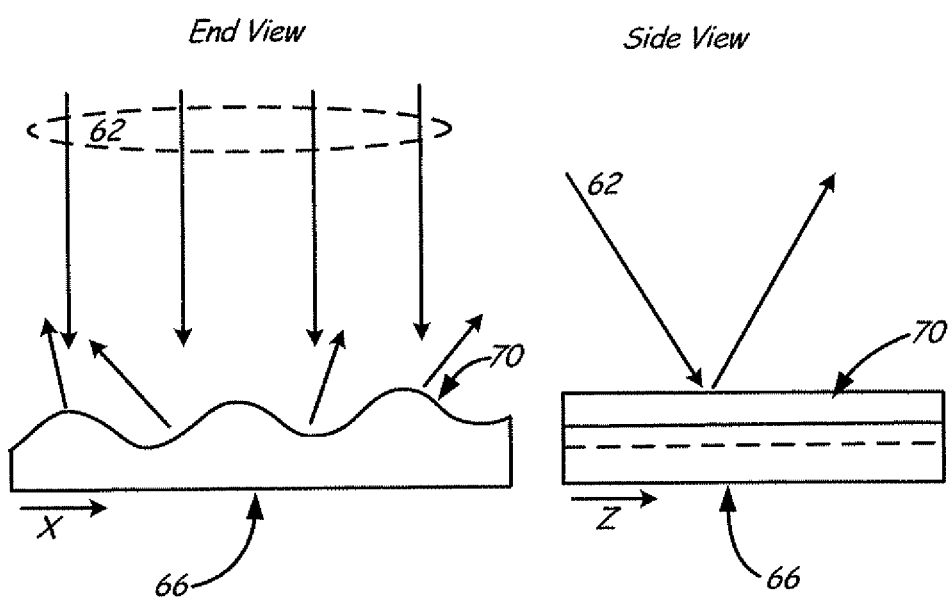
FIGS. 14A-B are cross sectional views of the reflective surface shown in FIG. 13.

FIGS. 13 and 14 illustrate an embodiment of the present invention with light pipe side walls which diffuse or scatter light in only one axis. In this embodiment it is preferred that the azimuth angles of the light bundle be spread on each reflection while maintaining elevation angles. This is achieved by adding curved or faceted, reflective surface 70 to the interior surface of light pipe side wall 66 as shown in FIG. 13. Cross sectional views of side wall 66 are shown in FIGS. 14A and 14B. FIG. 14A demonstrates how a collimated light ray bundle 62 is spread perpendicular to the axis of the cylindrical curvature on reflective surface 70. In FIG. 14B, the angle of reflection for light ray bundle 62 is maintained along the axis of the cylindrical curvature on reflective surface 70. Hence, the elevation angle of the source is maintained since the surface normal at every point of reflector 70 has no Z component. The curved, or faceted, surface of reflective surface 70 creates a range of new azimuth angles on every reflection over the entire surface of the light pipe wall 66 and therefore the azimuth angle of the source is rapidly randomized. Embodiments of the present invention can be practiced using any combination of refractive, diffractive and reflective surfaces for the interior surface of light pipe side wall 66.

In one aspect, reflective surface 70 is curved in segments of a cylinder. This spreads incoming light evenly in one axis, approximating a one-dimensional Lambertian surface, but does not spread light in the other axis. This shape is also easy to form in sheet metal. In another aspect, reflective surface 70 has a sine wave shape. However, since a sine wave shape has more curvature at the peaks and valleys and less curvature on the sides, the angular spread of light bundle 62 is stronger at the peaks and valleys than on the sides.

Figure 15A:
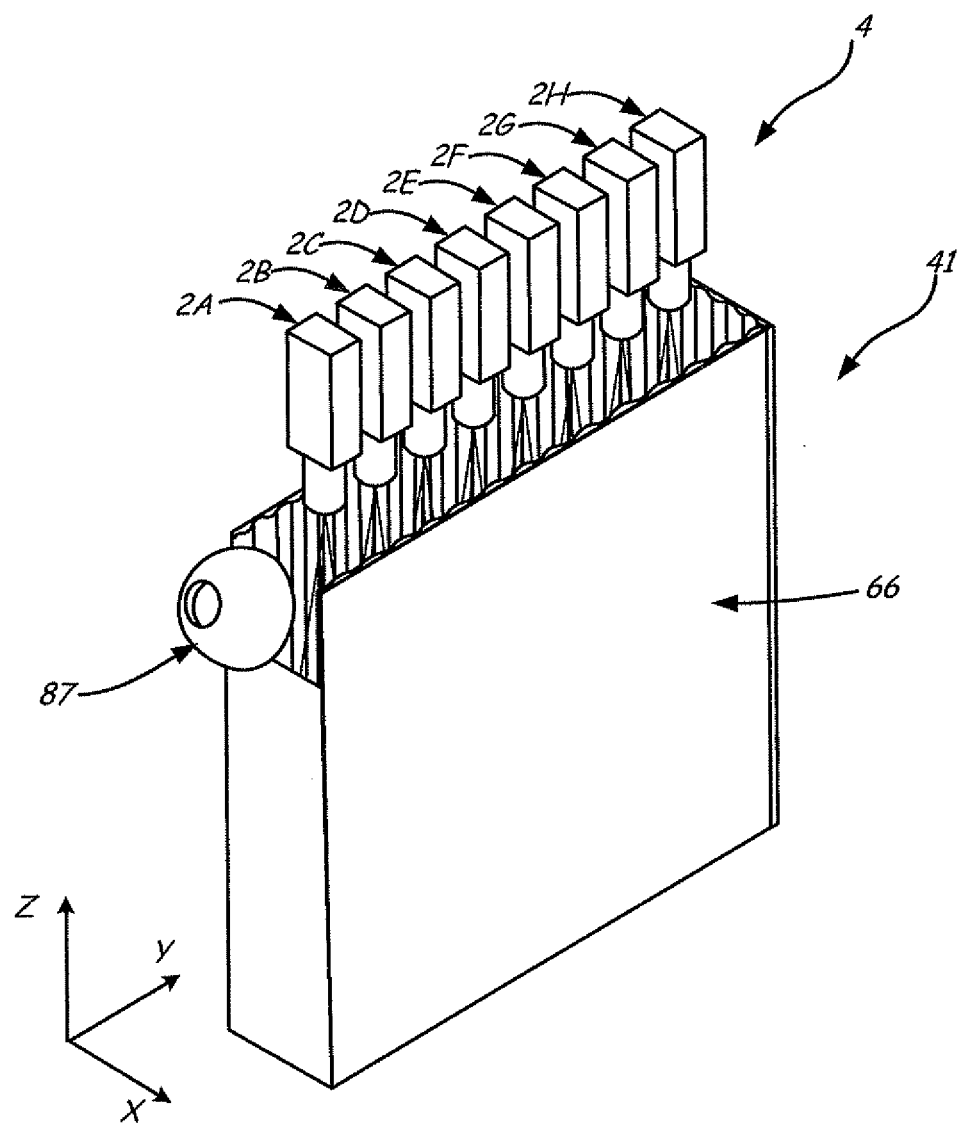
FIG. 15A is a perspective view of a light pipe illuminator and camera array in accordance with an embodiment of the present invention.
Figure 15B:
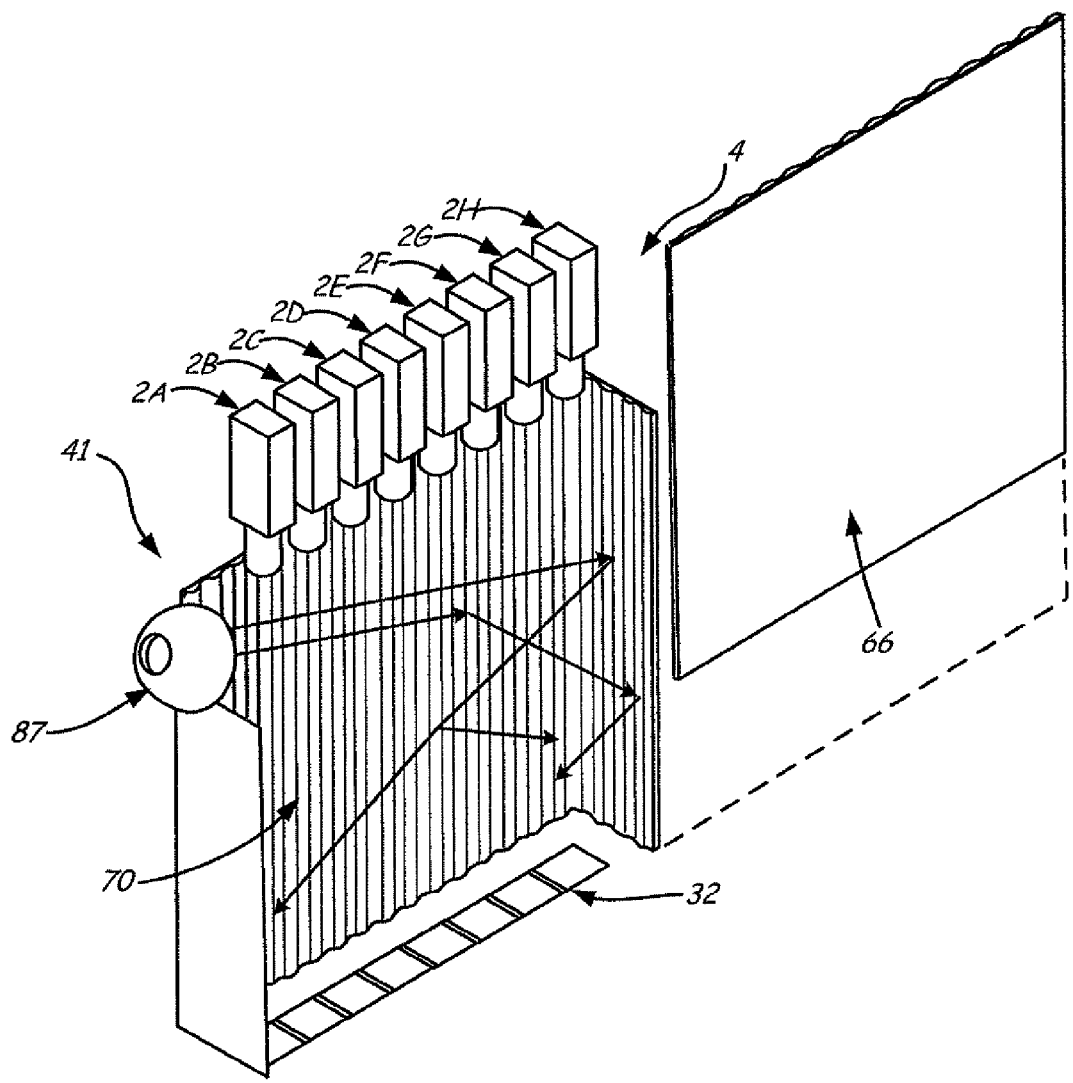
FIG. 15B is a cutaway perspective view of a light pipe illuminator and camera array in accordance with an embodiment of the present invention.
Figure 16:
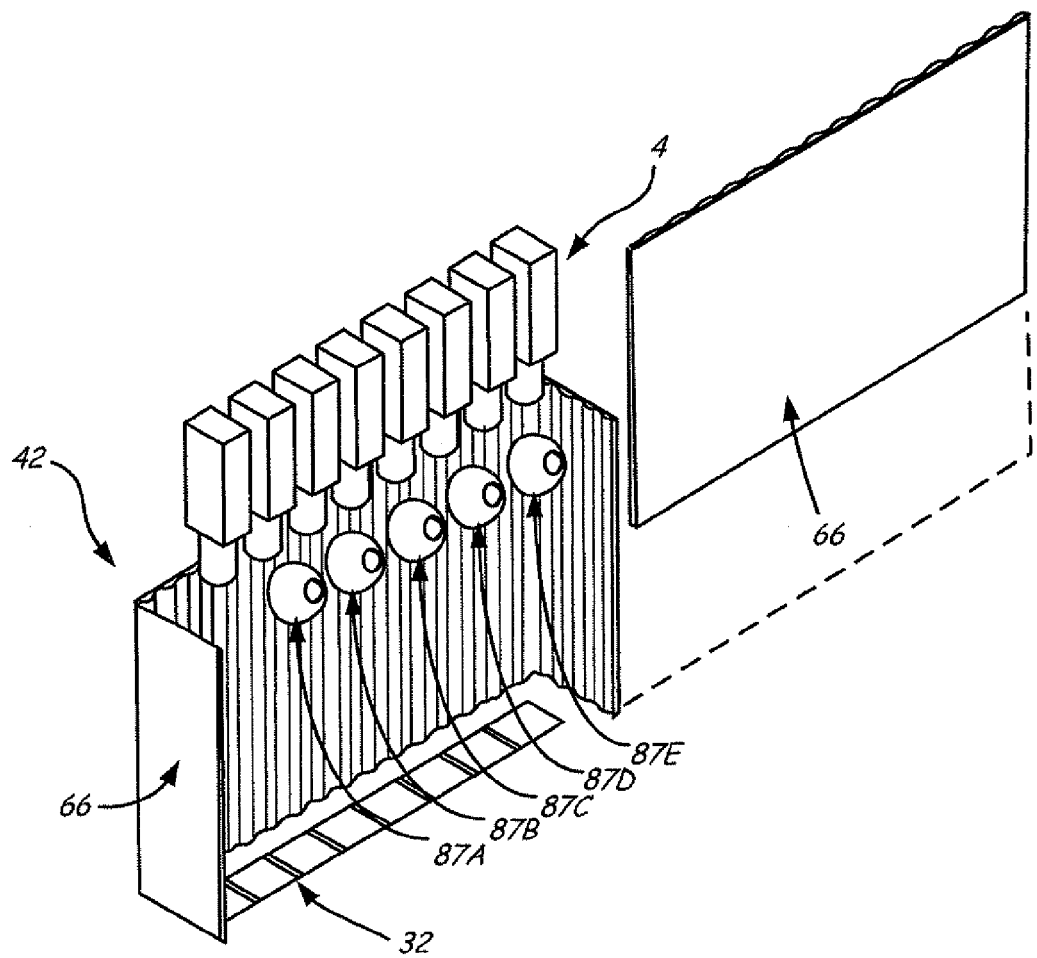
FIG. 16 is a cutaway perspective view of a camera array and illuminator with multiple sources in accordance with an embodiment of the present invention.

FIGS. 15A and 15B show the curved, reflective surfaces applied to the interior surfaces of light pipe illuminator 41 for camera array 4. Light pipe illuminator includes side walls 66 and light source 87. The one-dimensional diffusely reflecting surfaces 70 randomize azimuth angles more rapidly than a light pipe constructed of planar, reflective interior surfaces. This allows a more compact light pipe to be used which allows camera array 4 to be closer to the workpiece. FIG. 15B shows how light rays are randomized in azimuth angle after a small number of reflections.

Light pipe illuminator 42 (shown in FIG. 16) can be shortened in the Z direction compared to illuminator 41 if multiple light sources are used. Multiple sources, for example a row of collimated LEDs, reduce the total number of reflections required to achieve a spatially uniform source and hence reduce the required light pipe length. Illuminator 42 is illustrated with light sources 87A-87E which may also be strobed arc lamp sources.

Figure 17A:
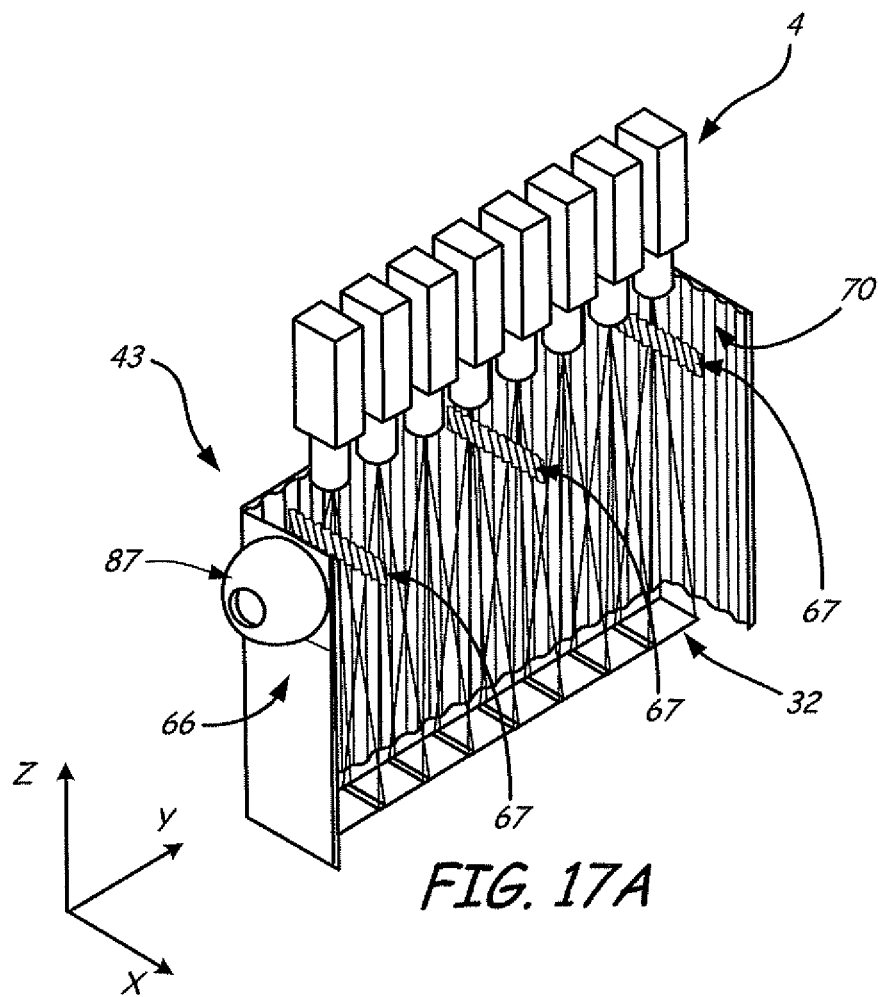
FIG. 17A is a perspective cutaway view of an illuminator and camera array in accordance with an embodiment of the present invention.
Figure 17B:
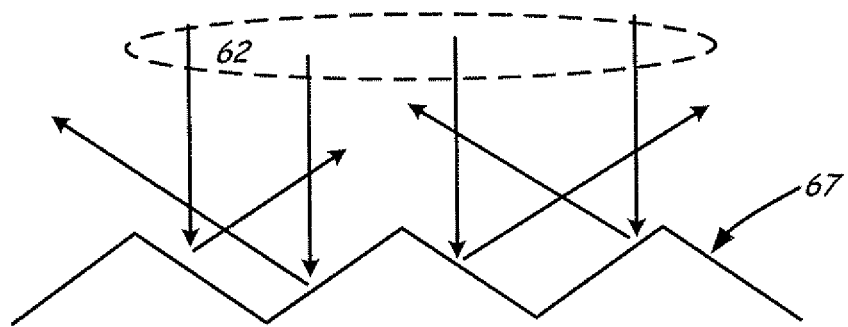
FIG. 17B is a cross sectional view of a chevron shaped mirror employed in accordance with an embodiment of the present invention.

In another aspect of the present invention shown in FIGS. 17A-17B, illuminator 43 includes mirrors 67 that reflect portions of the input beam from source 87 to the desired source elevation angle. Like the multiple source embodiment, this also results in a spatially uniform light field in a shorter light pipe. Mirrors 67 are placed between cameras to avoid blocking the view of the target and at different heights so that each mirror intercepts a portion of the light coming from source 67. Mirrors are shaped to reflect light at the desired elevation angle and toward light pipe side walls 66 where the curved, reflected surfaces 70 rapidly randomize the source azimuth direction. A cross sectional view of mirror 67 is shown in FIG. 17B. Mirror 67 may be, for example, a flat mirror that is formed into a series of chevrons.

Figure 18:
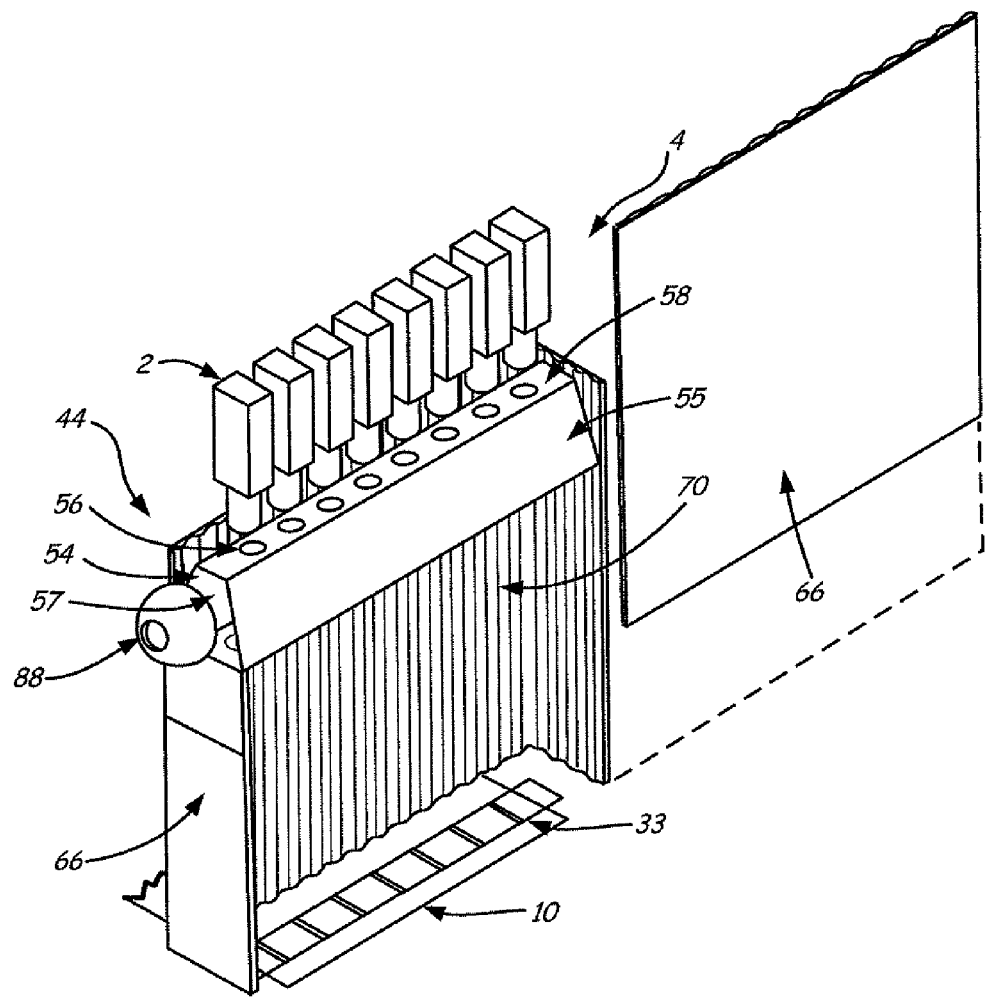
FIG. 18. is a cutaway perspective view of an illuminator and camera array in accordance with an embodiment of the present invention.
Figure 19:
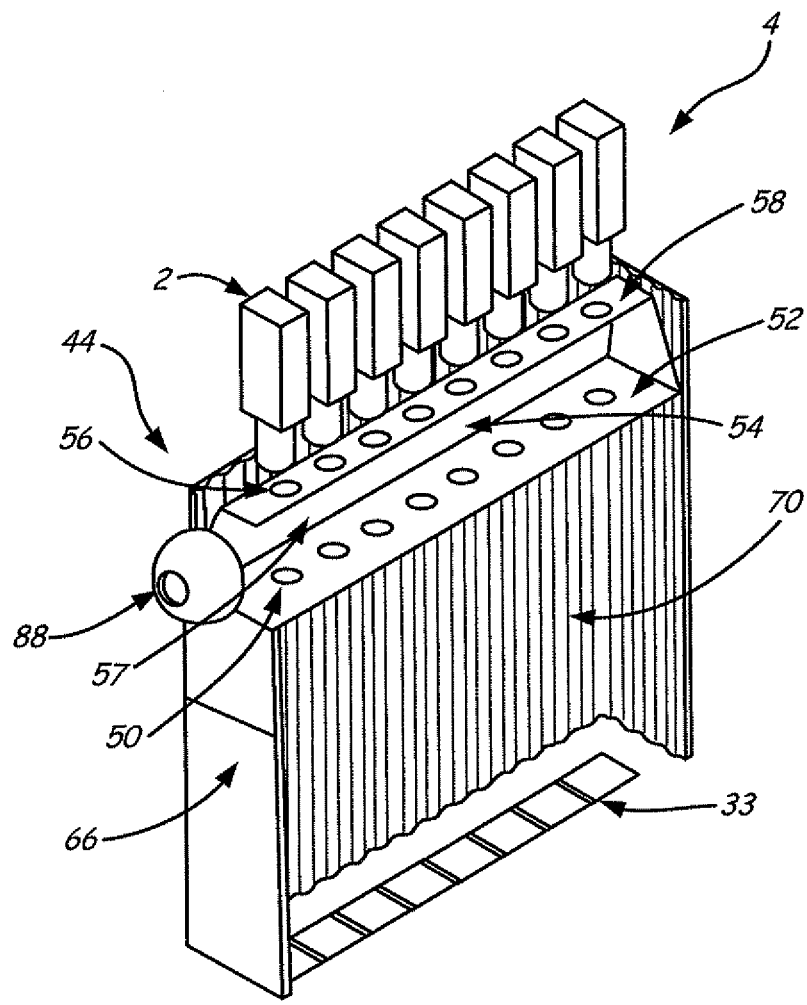
FIG. 19 is a second cutaway perspective view of the illuminator and camera array shown in FIG. 18.

In another embodiment of the present invention, FIGS. 18 and 19 illustrate illuminator 44 integrated with camera array 4. Light is injected by source 88 into light mixing chamber 57 defined by mirrors 54 and 55, top aperture plate 58, and diffuser plate 52. The interior surfaces of 54, 55, and 58 are reflective, whereas diffuser plate 52 is preferably constructed of a translucent, light diffusing material. Apertures 56 are provided on top plate 58 and apertures 50 are provided on diffuser plate 52 such that cameras 2 have an unobstructed view of the workpiece. In order to more clearly visualize diffuser plate 52 and apertures 50, mirror 55 has been removed in FIG. 19, compared with FIG. 18.

Figure 20:
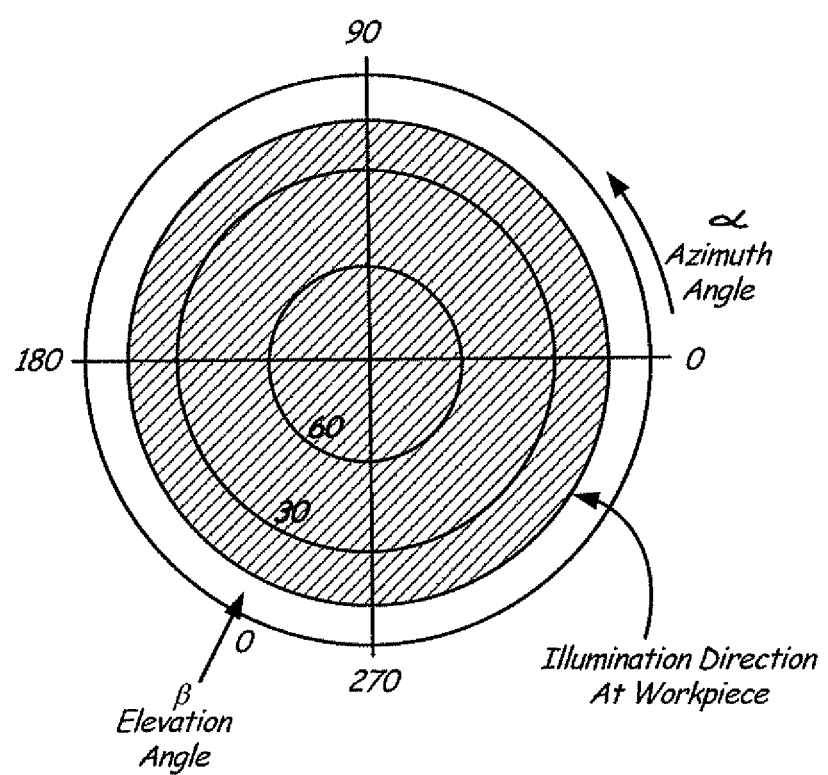
FIG. 20 is a polar plot of the illumination directions of the illuminator shown in FIGS. 18 and 19.

Light projected by source 88 is reflected by mirrors 54 and 55 and aperture plate 58. As the light reflects in mixing chamber 57, diffuser plate also reflects a portion of this light and is injected back into mixing chamber 57. After multiple light reflections within mixing chamber 57, diffuser plate 52 is uniformly illuminated. The light transmitted through diffuser plate 52 is emitted into the lower section of illuminator 44 which is constructed of reflective surfaces 70, such as those discussed with reference to FIGS. 13 and 14. Reflective surfaces 70 preserve the illumination elevation angle emitted by diffuser plate 52. The result is a spatially uniform illumination field at workpiece 10. FIG. 20 is a polar plot showing the output illumination directions of illuminator 44. Illuminator 44 creates an output light field, as shown in FIG. 20, which is termed cloudy day since illumination is nearly equal from almost all elevation and azimuth angles. The range of output elevation angles, however, can be controlled by the diffusing properties of diffuser plate 52.

Figure 21:
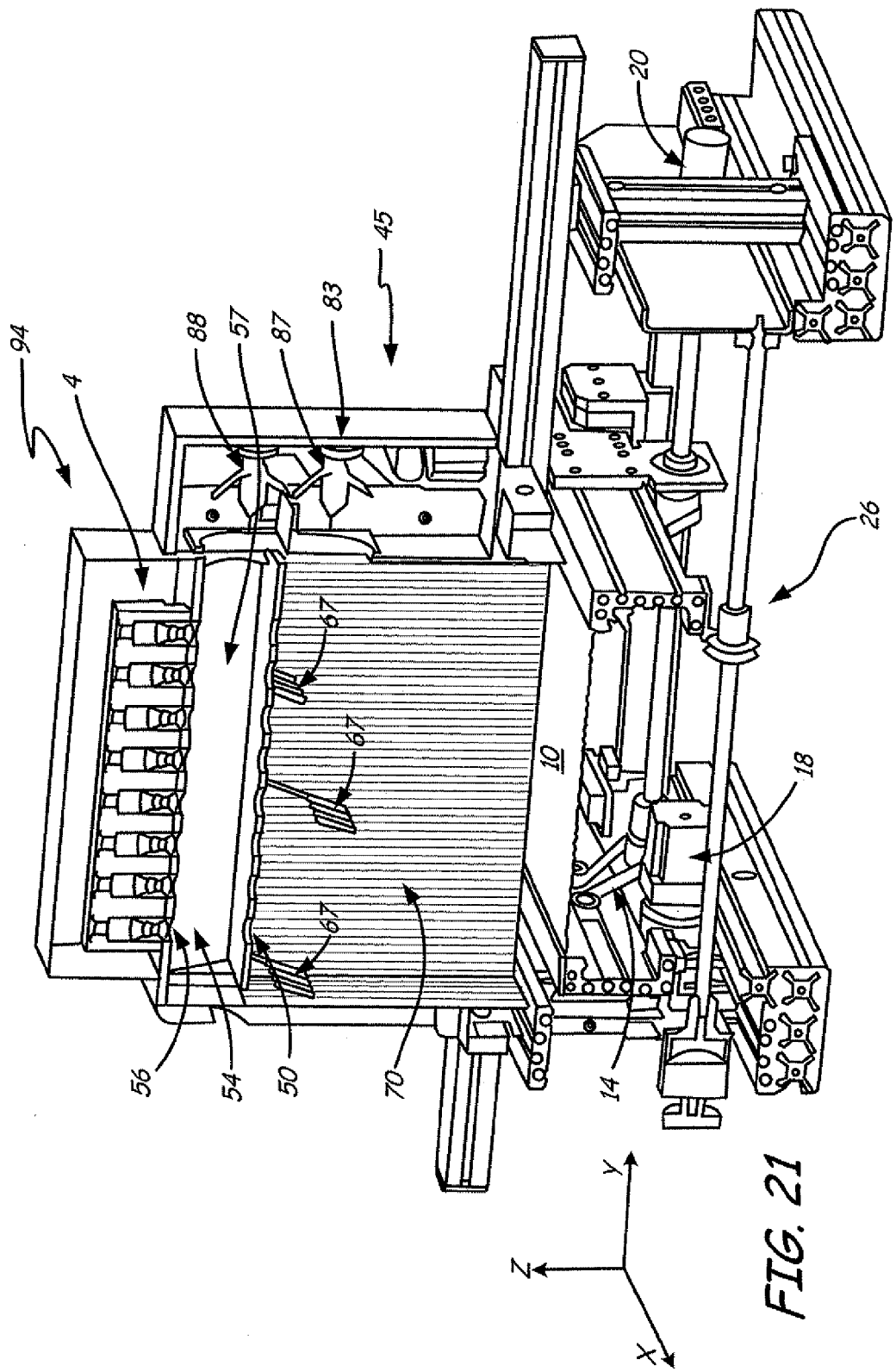
FIG. 21 is a cross-sectional perspective view of an inspection sensor in accordance with an embodiment of the present invention.
Figure 22:
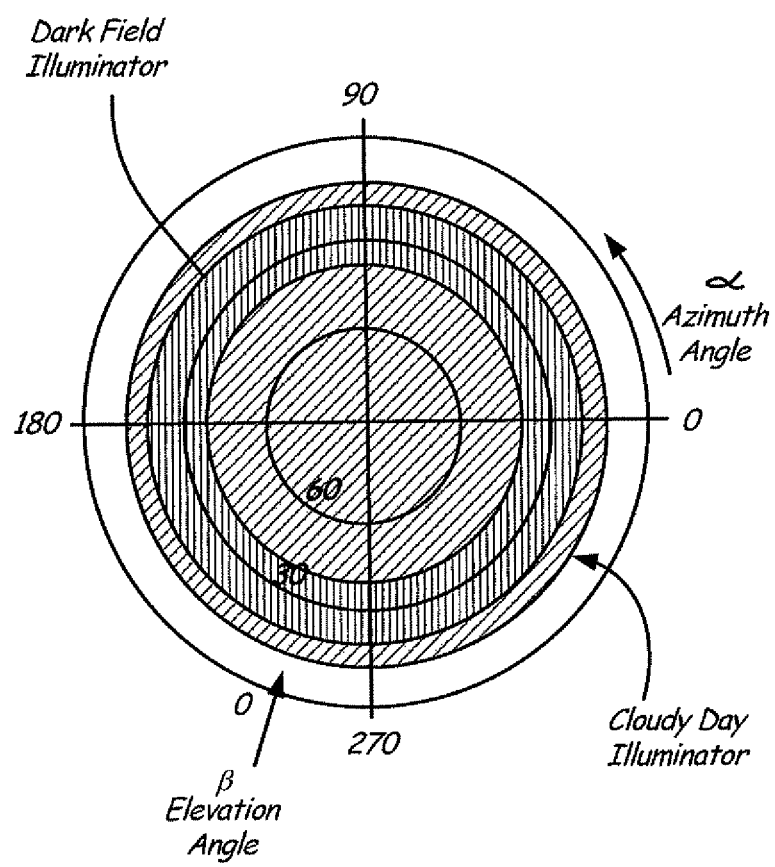
FIG. 22 is a polar plot of the illumination directions of the illuminator shown in FIG. 21.

FIG. 21 shows a preferred embodiment of optical inspection sensor 94. Optical inspection sensor 94 includes camera array 4 and integrated illuminator 45. Illuminator 45 facilitates independently controlled cloudy day and dark field illumination. A dark field illumination field is produced on printed circuit board 10 by energizing light source 87. A cloudy day illumination field is projected onto printed circuit board 10 by energizing light source 88. FIG. 22 shows the polar plot and illumination directions for the cloudy day and dark field illuminations. In one aspect, sources 87 and 88 are strobed to suppress motion blurring effects due to the transport of circuit board 10 in a non-stop manner.

It is understood by those skilled in the art that the image contrast of various object features vary depending on several factors including the feature geometry, color, reflectance properties, and the angular spectrum of illumination incident on each feature. Since each camera array field of view may contain a wide variety of features with different illumination requirements, embodiments of the present invention address this challenge by imaging each feature and location on workpiece 10 two or more times, with each of these images captured under different illumination conditions and then stored into a digital memory. In general, the inspection performance may be improved by using object feature data from two or more images acquired with different illumination field types.

It should be understood that embodiments of the present invention are not limited to two lighting types such as dark field and cloudy day illumination field nor are they limited to the specific illuminator configurations. The light sources may project directly onto workpiece 10. The light sources may also have different wavelengths, or colors, and be located at different angles with respect to workpiece 10. The light sources may be positioned at various azimuthal angles around workpiece 10 to provide illumination from different quadrants. The light sources may be a multitude of high power LEDs that emit light pulses with enough energy to "freeze" the motion of workpiece 10 and suppress motion blurring in the images. Numerous other lighting configurations are within the scope of the invention including light sources that generate bright field illumination fields or transmit through the substrate of workpiece 10 to backlight features to be inspected.

Successful inspection of small component and printed circuit board features requires a fine pixel pitch, high quality lenses and illumination, as well as precise focus. However, warp of the printed circuit board may make it difficult to use a single focus setting over the entire circuit board and maintain high resolution imagery. Circuit boards warped by up to 8 mm have been observed. Adaptive focus of the cameras enables precise focus as the printed circuit board and optical inspection sensor move in continuous relative motion with respect to each other. Two capabilities to adaptively focus the cameras are required. The first capability is a relative or absolute measurement of the range to the printed circuit board. The second capability is a motion system to refocus the cameras to the required range before each image capture while the circuit board and optical inspection sensor move relative to each other.

Referring back to FIGS. 2 and 4, camera array field of view 32 consists of overlapping camera fields of view 32A-32H. The overlap regions between camera fields of view 32A-32H decrease as circuit board 10 is positioned closer to camera array 4. Conversely, the overlap regions between camera fields of view 32A-32H increase as circuit board 10 is positioned further away from camera array 4. If circuit board 10 is warped, the amount of overlap, or stereo disparity, between camera fields of view 32A-32H will vary based on the range to circuit board 10 in the local overlap regions. Range to the circuit board or workpiece may be computed by measuring the stereo disparity between the fields of view of the camera array. Stereo vision systems are well known. Examples of computing range from stereo disparity can be found in "A Taxonomy and Evaluation of Dense Two-Frame Stereo Correspondence Algorithms" by Scharstein and Szeliski and "A Space-Sweep Approach to True Multi-Image Matching" by Robert T. Collins.

Figure 23:
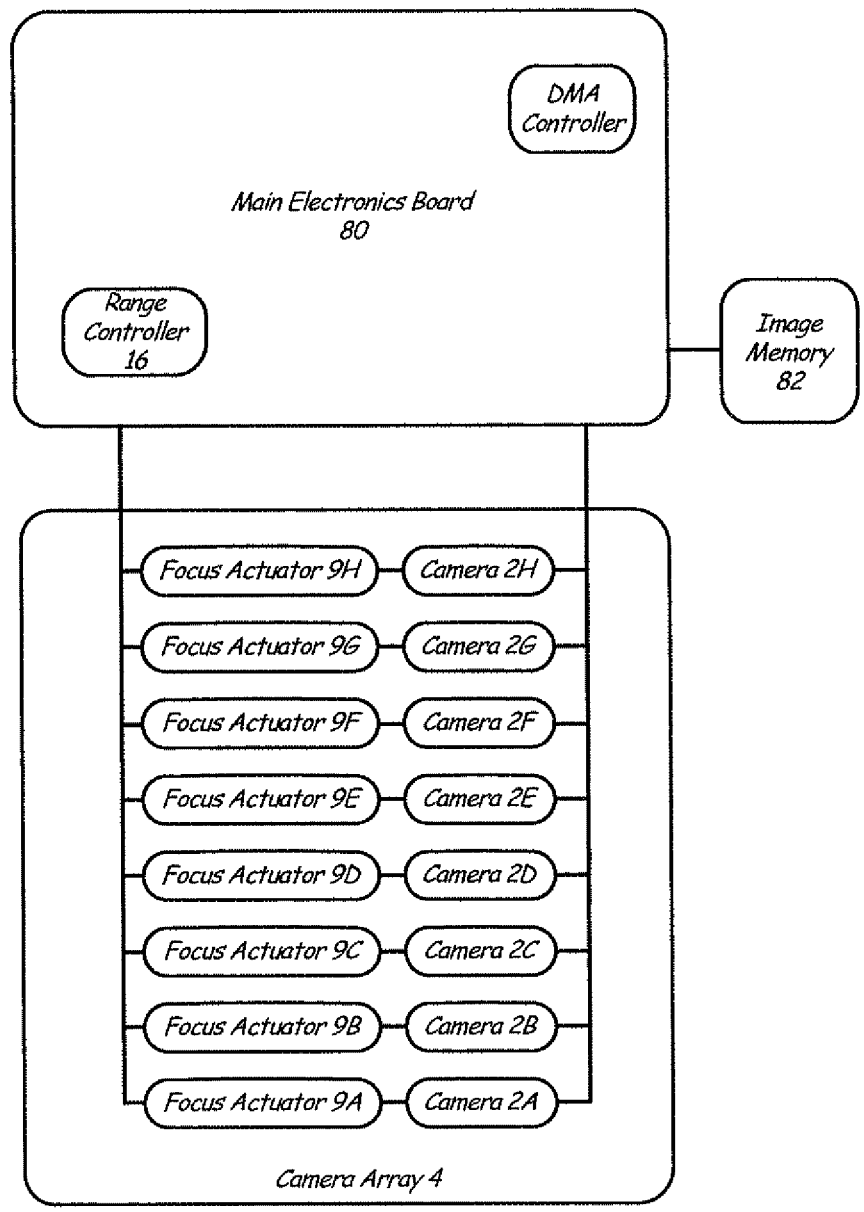
FIG. 23 is a block diagram of a portion of an optical inspection sensor in accordance with an embodiment of the present invention.

FIG. 23 is a block diagram of a portion of an optical inspection sensor. Main electronics board 80 includes range calculator 16. Range calculator 16 receives image data from cameras 2A-2H and calculates the stereo disparity in the overlap regions between each camera field of view 30A-30H to compute range. Focus actuators 9A-9H may adjust the position of the detectors in cameras 2A-2H to maintain nominal focus based on signals from range calculator 16. Alternatively, the lens assembly, individual lens elements, or the entire cameras 2A-2H may be driven by focus actuators 9A-9H to maintain focus. Autofocus actuators are well known in the prior art. An example autofocus actuator is disclosed in U.S. Pat. No. 7,285,879.

Figure 24:
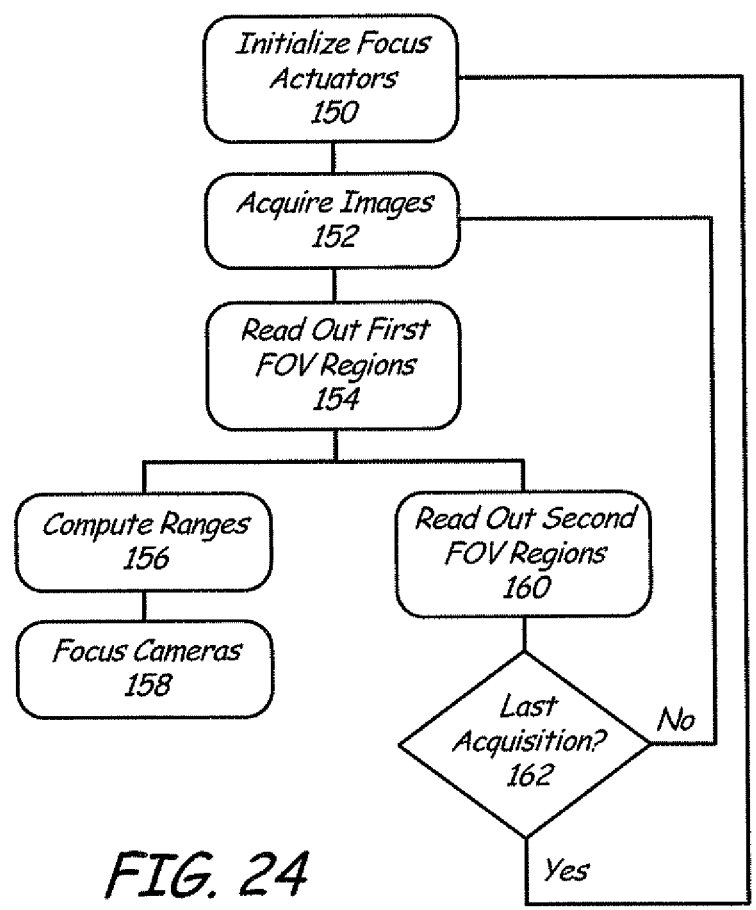
FIG. 24 is a flowchart of a method for adaptively focusing a camera array in accordance with an embodiment of the present invention.

FIG. 24 is a flowchart for adaptively focusing cameras 2A-2H based on calculating the range from the stereo disparity between camera fields of view 30A-30H. Prior to the image acquisition sequence at step 150, focus actuators 9A-9H are initialized by main electronics board 80 to focus cameras 2A-2H at their nominal focus positions. At step 152, images are acquired at the appropriate location on circuit board 10 and with the appropriate illumination. At step 154, the first region of each camera field of view is read out and transferred to range calculator 16 and also to image memory 82. In one embodiment, each camera 2A-2H has 2592 pixels in the Y direction and 1944 lines of pixels in the X direction. In this embodiment, the first field of view regions consist of the first 400 video lines from each camera 2A-2H and the second field of view regions consist of the remaining 1544 video lines from each camera. Range calculator 16 calculates range to circuit board 10 from the stereo disparity in the first field of view overlap regions in step 156. Cameras 2A-2H are focused in step 158 when main electronics board 80 sends signals to focus actuators 9A-9H based on the ranges calculated at step 156. This adaptive focus step accommodates changes in the range to the local areas of circuit board 10 as it is translated by conveyor 26. Step 160 starts immediately after step 154 to read the remaining video lines from each camera. If the image acquisition sequence for circuit board 10 is complete at step 162, then the control is returned to step 150 where the cameras are returned to their nominal focus positions. Otherwise, control is returned to step 152 to acquire the next images.

Figure 25:
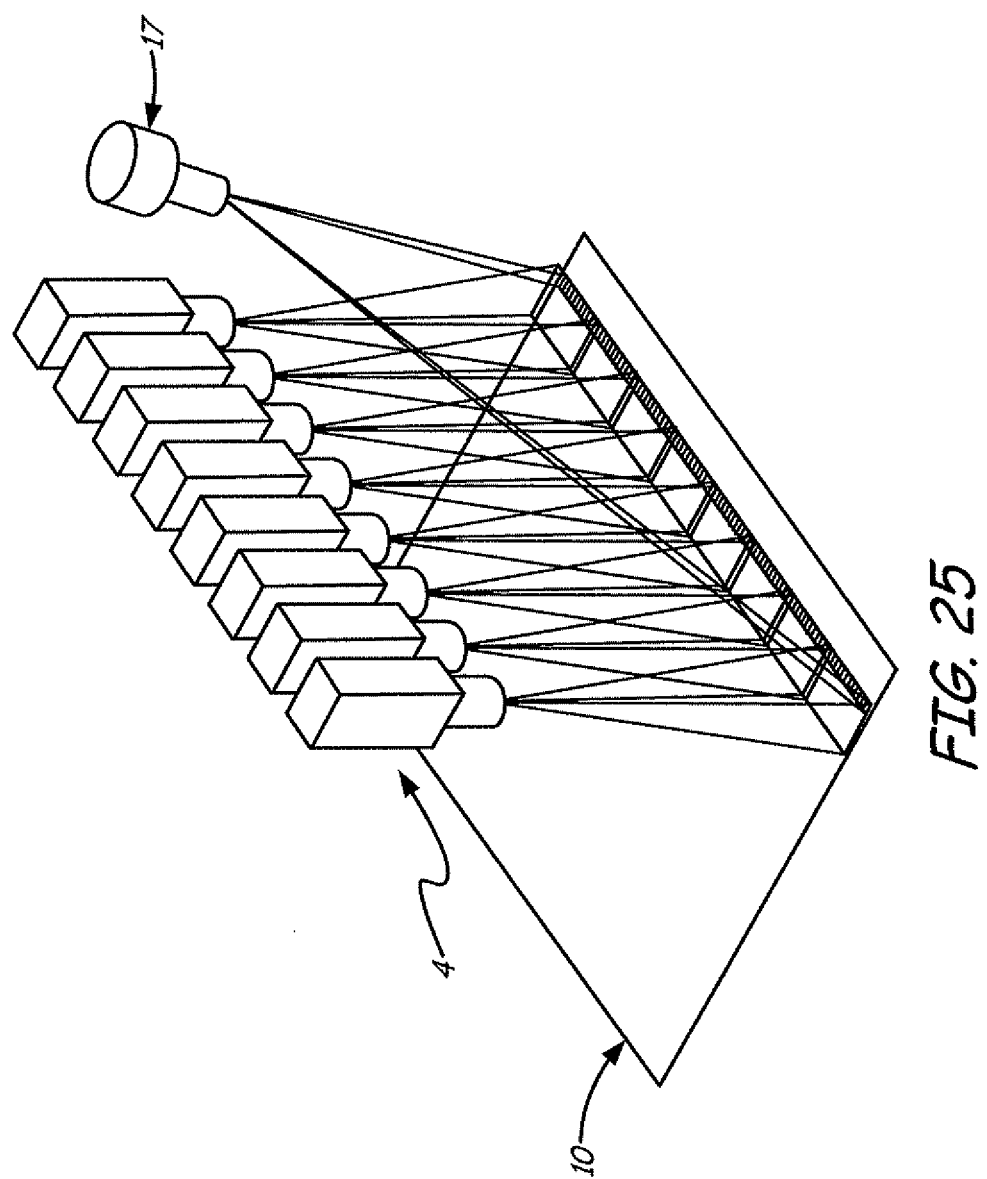
FIG. 25 is a perspective view of a camera array and stripe projector in accordance with an embodiment of the present invention
Figure 26:
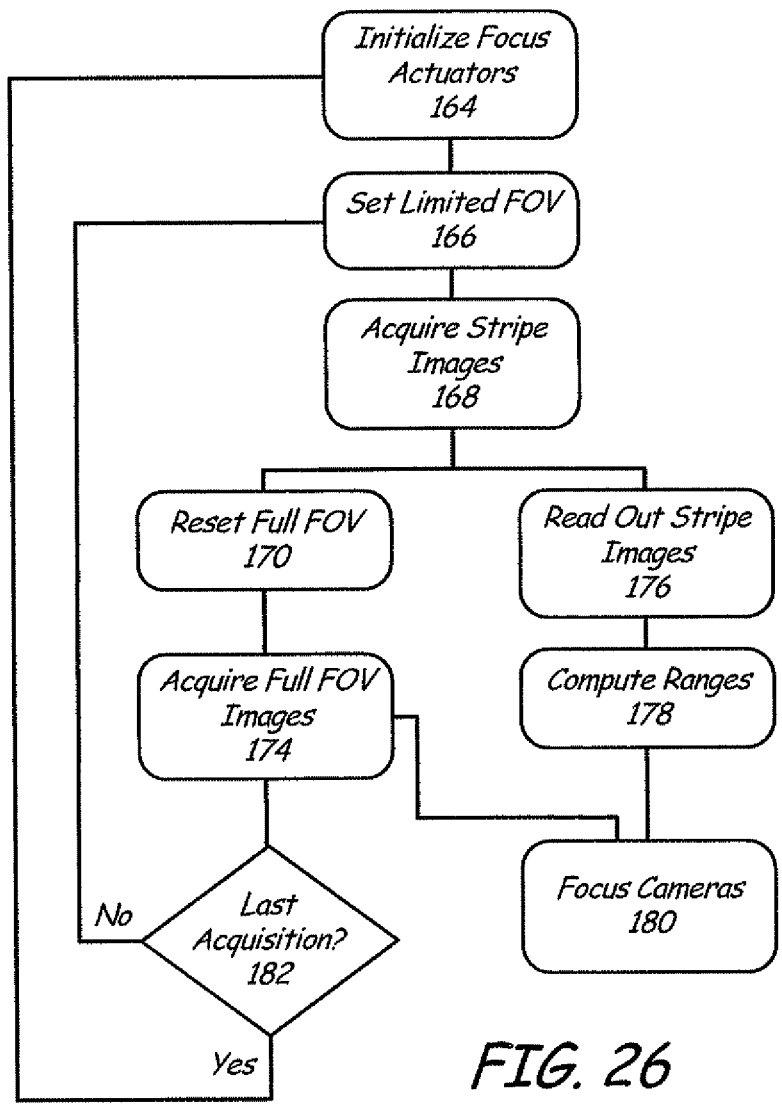
FIG. 26 is a flowchart of a method for adaptively focusing a camera array in accordance with an embodiment of the present invention.

FIG. 25 is a perspective view of a camera array 4 and stripe projector 17 for providing range information to range calculator 16. The cloudy day and darkfield illuminators have been removed from FIG. 25 for clarity. Stripe projector 17 projects a pattern of stripes onto circuit board 10 from a different angle than the viewing angle of camera array 4. As the range to circuit board 10 varies the stripe positions will shift. It is understood that other structured patterns of light may also be projected to permit the range to circuit board 10 to be calculated. FIG. 26 is a flowchart for adaptively focusing cameras 2A-2H based on calculating the range from the stripe pattern. Prior to the image acquisition sequence at step 164, focus actuators 9A-9H are initialized by main electronics board 80 to focus cameras 2A-2H at their nominal focus positions. At step 166 the detectors in cameras 2A-2H are configured to read out a limited field of view. In this embodiment where each detector has 2592 pixels in the X direction and 1944 lines of pixels in the Y direction, the limited field of view regions consist of the first 100 video lines from each detector in cameras 2A-2H. Images of the stripe pattern are acquired at step 168. The stripe images are read out of cameras 2A-2H by main electronics board 80 in step 176 and the range to circuit board 10 is calculated by range calculator 16 at step 178.

As the stripe images are being read out in step 176, the detectors in cameras 2A-2H are configured to read out the entire field of view. At step 174, images are acquired at the appropriate location on circuit board 10 and with the appropriate illumination. Step 180 starts after completion of steps 174 and 178. Cameras 2A-2H are focused in step 180 when main electronics board 80 sends signals to focus actuators 9A-9H based on the ranges calculated at step 178 to accommodate changes in the range to the local areas of circuit board 10 as it is translated by conveyor 26. If the image acquisition sequence for circuit board 10 is complete at step 182, then the control is returned to step 164 where the cameras are returned to their nominal focus positions. Otherwise, control is returned to step 166 to prepare for the acquisition of the next stripe images.

Figure 27:
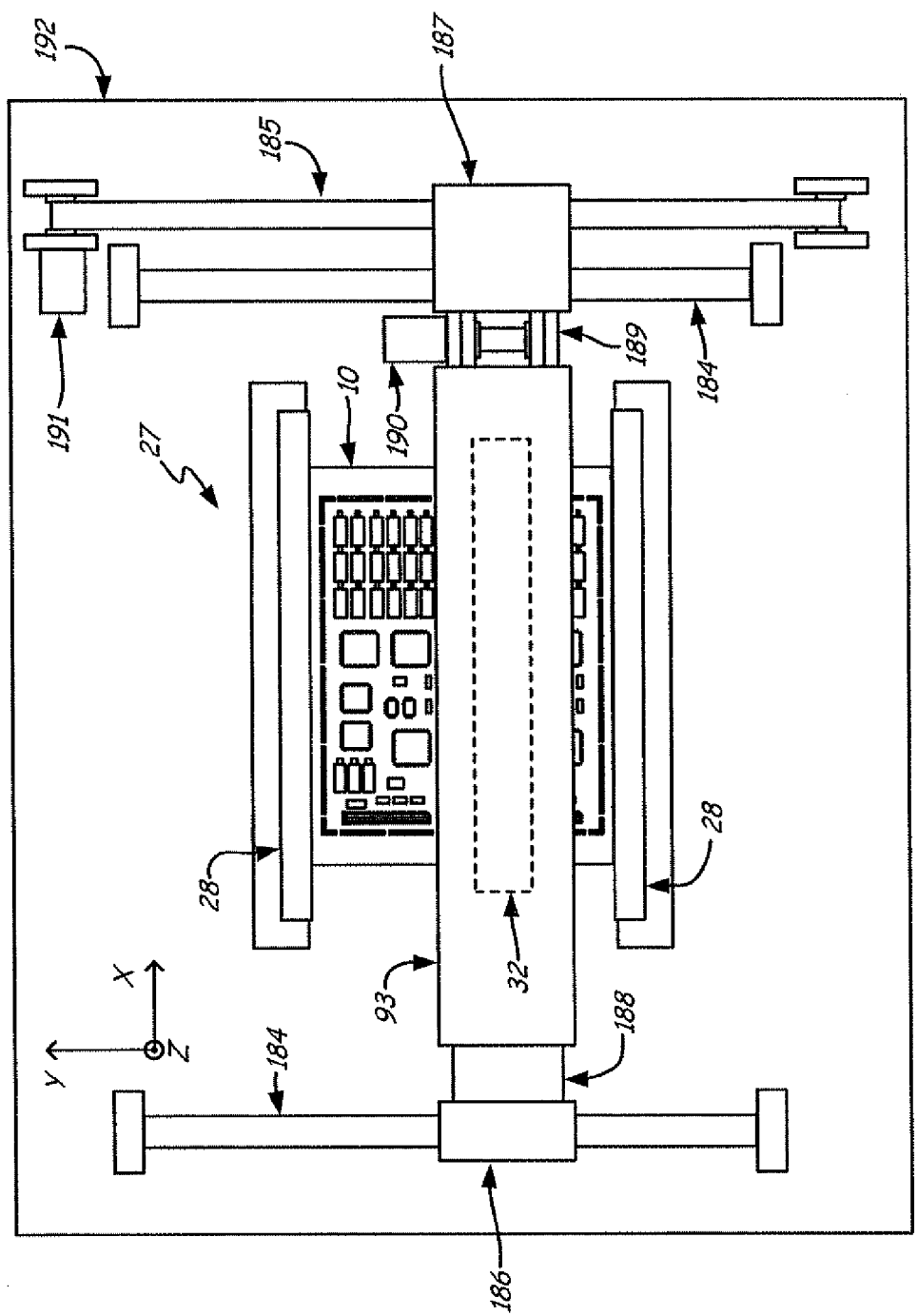
FIG. 27 is a top plan view of an optical inspection sensor that translates relative to a fixed workpiece in accordance with an embodiment of the present invention.

FIG. 27 is a top plan view of an adaptively focusing inspection system in accordance of another embodiment of the present invention. Optical inspection sensor 93 is disposed above base 192 and translates relative to circuit board 10. Circuit board 10 is supported by transport conveyor 27 and held rigidly with board edge clamps 28. Supports 186 and 187 are movable on rails 184. Motor 191, coupled to belt 185, drives support 187 to move inspection sensor 93 in the Y direction. Inspection sensor 93 is capable of generating multiple illumination field types and includes a camera array with camera array field of view 32 for one of the illumination field types. Range to circuit board 10 may be calculated measuring the disparity in the field of view overlap regions of camera array field of view 32. Alternatively, optical inspection sensor 93 may include a structured light projector such as that discussed with respect to FIG. 25 in order to calculate range to circuit board 10 or optical inspection sensor 93 may include one or more independent range sensors such as those commonly referred to as laser displacement sensors. U.S. Pat. No. 6,288,786 discloses an example laser displacement sensor.

Clamping circuit board 10 by its edges eliminates much of the warp in the X direction so that the range varies mainly in the Y direction and range will be relatively constant for each camera at a given Y position of optical inspection sensor 93. This simplifies the adaptive focus requirements so that a single focus actuator may be used. This focus actuator may adjust position of all cameras in unison by mounting all cameras fixedly with respect to each other. In another embodiment, optical inspection sensor 93 may translated in the Z direction to maintain focus during the image acquisition sequence. As shown in FIG. 27, slide 188 is rigidly attached to support 186 and stage 189 translates optical inspection sensor 93 in the Z direction by energizing motor 190. Adaptive focus is achieved by positioning stage 189 based on range to circuit board 10.

Figure 28A:
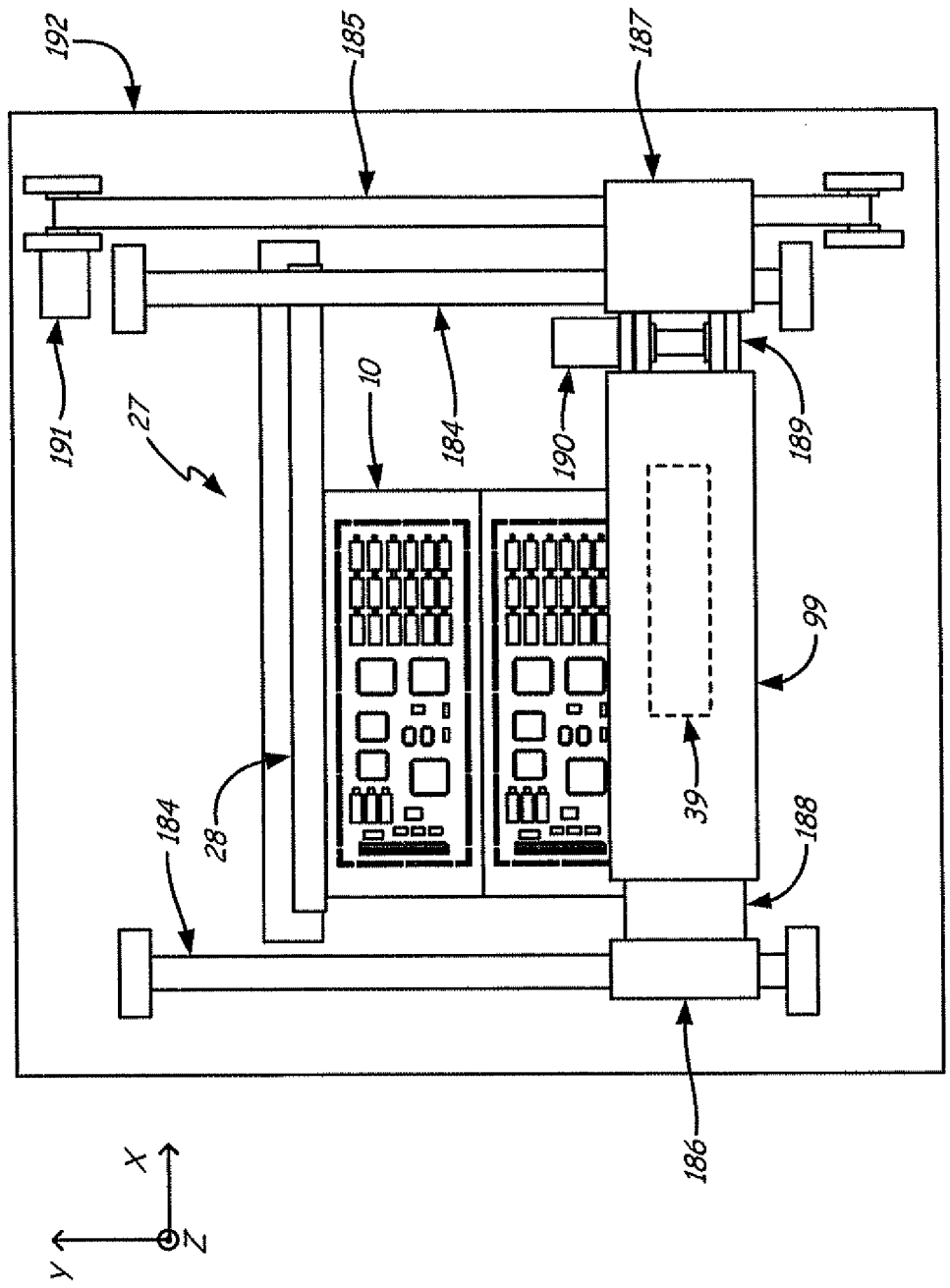
FIG. 28A is a top plan view of an optical inspection sensor that acquires images of a portion of a workpiece in accordance with an embodiment of the present invention.
Figure 28B:
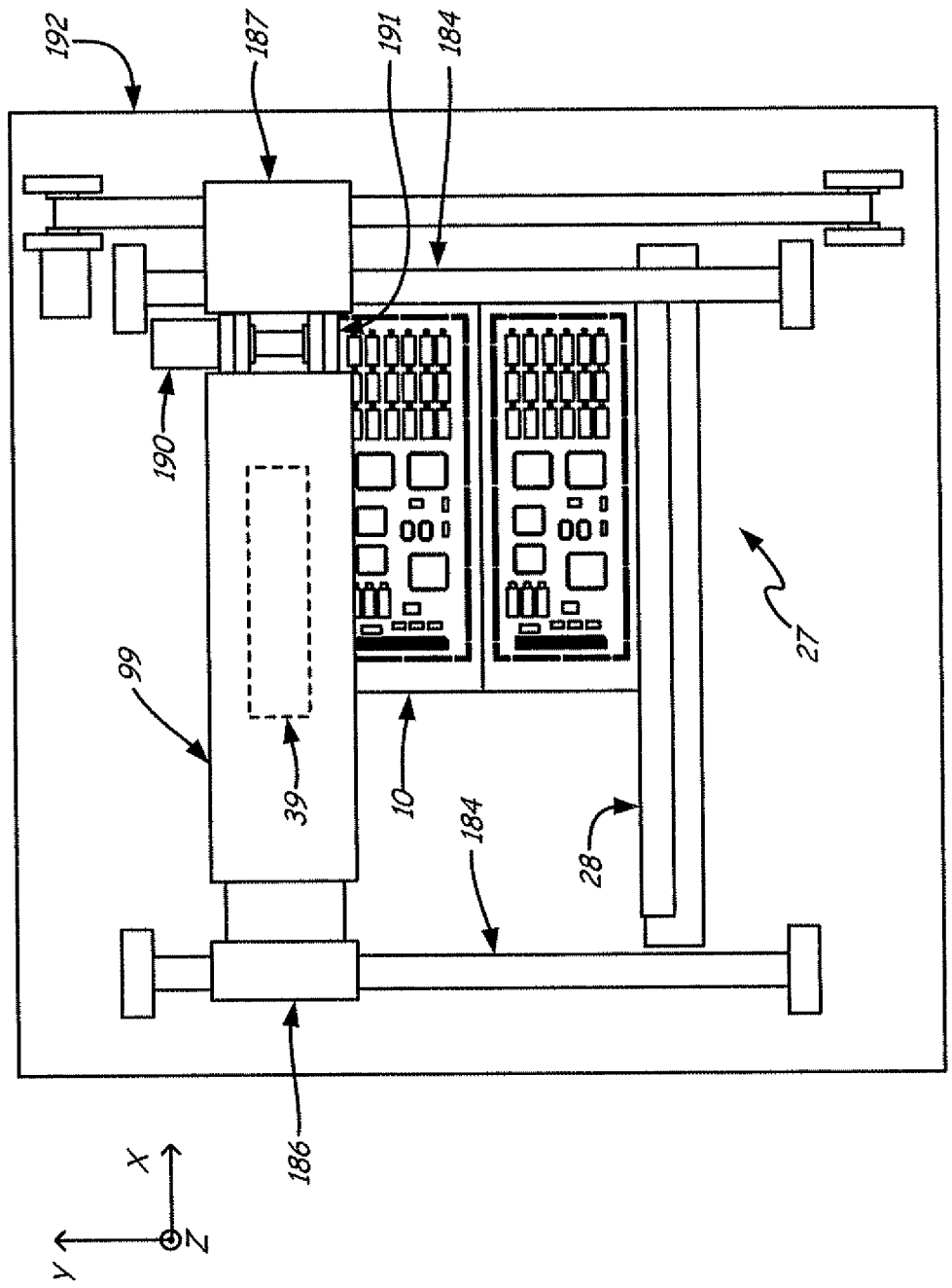
FIG. 28B is a top plan view of the optical inspection sensor and workpiece of FIG. 28A positioned to acquire images of the remaining portions of the workpiece in accordance with an embodiment of the present invention.

FIG. 28A is a top plan view of an embodiment that includes optical inspection sensor 99 with camera array field of view 39 for one illumination field type. The width of camera array field of view 39 is narrower than the width of circuit board 10. Optical inspection sensor 99 is adaptively focused as it translates in the positive Y direction to acquire images of a portion of circuit board 10. Clamps 28 release circuit board 10 and it is indexed in the X direction as shown in FIG. 28B. Circuit board 10 is then clamped again. Optical inspection sensor 99 is adaptively focused as it translates in the negative Y direction to acquire images of the remaining portion of circuit board 10.

Although the present invention has been described with reference to preferred embodiments, workers skilled in the art will recognize that changes may be made in form and detail without departing from the spirit and scope of the invention.

What is claimed is:

1. An optical inspection system for inspecting a substrate, the system comprising:
    an array of cameras configured to acquire a plurality of sets of images as the substrate and the array undergo relative motion with respect to each other;
    at least one focus actuator operably coupled to each camera of the array of cameras to cause displacement of at least a portion of each camera that affects focus;
    a substrate range calculator configured to receive at least portions of images from the array and calculate range between the array of cameras and the substrate; and
    a controller coupled to the array of cameras and to the range calculator, the controller being configured to provide a control signal to each of the at least one focus actuator to adaptively focus each camera of the array during the relative motion.

2. The optical inspection system of claim 1, wherein the at least one focus actuator includes a plurality of focus actuators equal in number to a number of cameras in the array, such that each camera of the array has its own focus actuator.

3. The optical inspection system of claim 2, wherein each focus actuator is configured to move an image detector of its respective camera.

4. The optical inspection system of claim 2, wherein each focus actuator is configured to move a lens element.

5. The optical inspection system of claim 2, wherein each focus actuator is configured to move a lens.

6. The optical inspection system of claim 2, wherein each focus actuator is configured to move its respective camera.

7. The optical inspection system of claim 1, wherein the at least one focus actuator is configured to move the entire array of cameras.

8. The optical inspection system of claim 1, wherein the range calculator computes ranges based on stereo disparity in overlap regions of images acquired by different but adjacent cameras.

9. The optical inspection sensor of claim 1, and further comprising a structured light projector disposed to project a structured light pattern on the substrate.

10. The optical inspection system of claim 9, wherein the structured light pattern is configured as a series of stripes.

11. The optical inspection system of claim 10, wherein the range calculator computes range based upon a position of the stripes in acquired images.

12. The optical inspection system of claim 1, wherein array of cameras undergoes motion relative to the fixed substrate.

13. The optical inspection system of claim 1, wherein the substrate undergoes motion relative to the fixed array of cameras.

14. A method for inspecting a substrate, the method comprising:
  providing an array of cameras configured to acquire images of the substrate while the substrate and the array of cameras undergo relative motion with respect to each other;
  computing range between the array of cameras and the substrate;
  adjusting focus of at least one camera of the array of cameras and acquiring a set of images with the array of cameras after adjusting focus; and
  processing the set of images to determine an inspection result relative to the substrate.

15. The method of claim 14, wherein range is computed using stereo disparity between adjacent, and different images.

16. The method of claim 14, wherein range is computed using a structured illumination projector to project a structured illumination pattern on the substrate.

17. The method of claim 16, wherein the structured illumination pattern is configured as a series of stripes.

18. The method of claim 14, wherein range is calculated by reading out a subset of a field of view of each camera of the array of cameras.

19. The method of claim 14, wherein adjusting focus includes driving a plurality of focus actuators relative to respective cameras based on the computed range.

20. The method of claim 14, wherein adjusting focus includes moving a detector of at least one camera.

21. The method of claim 14, wherein adjusting focus includes moving a lens element.

22. The method of claim 14, wherein adjusting focus includes moving a lens.

23. The method of claim 14, wherein adjusting focus includes moving an entire camera.

24. The method of claim 14, wherein adjusting focus includes moving the entire array of cameras.

25. The method of claim 14, wherein adjusting focus includes moving an optical inspection sensor.

26. The method of claim 14, wherein the relative motion includes moving the array of cameras relative to the fixed substrate.

27. The method of claim 26, wherein the images are of a portion of the substrate.

28. The method of claim 27, wherein the substrate is moved to a new, fixed location and additional images are acquired while the array of cameras moves relative to the fixed substrate at the new location.

* * * * *